US012560491B2

(12) United States Patent
Diller et al.

(10) Patent No.: US 12,560,491 B2
(45) Date of Patent: Feb. 24, 2026

(54) TWO-DIMENSIONAL RESISTANCE TEMPERATURE DETECTORS AND RELATED METHODS FOR DETERMINING AVERAGE TEMPERATURE OVER A SURFACE

(71) Applicant: BOARD OF REGENTS, THE UNIVERSITY OF TEXAS SYSTEM, Austin, TX (US)

(72) Inventors: Kenneth R. Diller, Elgin, TX (US); Sepideh Khoshnevis, Austin, TX (US); Laura Hemmen, Lakeway, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 434 days.

(21) Appl. No.: 18/021,664

(22) PCT Filed: Aug. 20, 2021

(86) PCT No.: PCT/US2021/046818

§ 371 (c)(1),
(2) Date: Feb. 16, 2023

(87) PCT Pub. No.: WO2022/040492

PCT Pub. Date: Feb. 24, 2022

(65) Prior Publication Data

US 2023/0392993 A1 Dec. 7, 2023

Related U.S. Application Data

(60) Provisional application No. 63/068,776, filed on Aug. 21, 2020.

(51) Int. Cl.
*G01K 7/04* (2006.01)
*A41D 1/00* (2018.01)
(Continued)

(52) U.S. Cl.
CPC ............... *G01K 7/183* (2013.01); *G01K 3/06* (2013.01); *G01K 13/20* (2021.01); *H05K 1/038* (2013.01);
(Continued)

(58) Field of Classification Search
CPC .......... G01K 3/06; G01K 7/183; G01K 13/20; G01K 7/04; G01K 2213/00; A41D 1/002;
(Continued)

(56) References Cited

U.S. PATENT DOCUMENTS 2,957,153 A 10/1960 Engellard
4,371,483 A 2/1983 Mattson
(Continued)

FOREIGN PATENT DOCUMENTS

CN 116288892 A * 6/2023 ............. D04B 1/102
KR 101518173 B1 * 5/2015 ............. H10N 10/01

OTHER PUBLICATIONS

Computer translation of CN_116288892 (Year: 2025).*
(Continued)

*Primary Examiner* — Randy W Gibson
(74) *Attorney, Agent, or Firm* — Meunier Carlin & Curfman LLC

(57) ABSTRACT

A two-dimensional resistance temperature detector for determining average temperature over a surface may include a continuous length of insulated wire having a first end and a second end. The insulated wire may be arranged to form a mesh structure with respective sections of the insulated wire overlapping and contacting one another. A method for determining average temperature over a surface may include positioning a two-dimensional resistance temperature detector over the surface such that an insulated wire of the two-dimensional resistance temperature detector directly contacts the surface, determining a resistance of the insu-
(Continued)

lated wire, and determining an average surface temperature based at least in part on the resistance of the insulated wire. The insulated wire may be arranged to form a mesh structure with respective sections of the insulated wire overlapping and contacting one another.

20 Claims, 20 Drawing Sheets

(51) Int. Cl.
| | |
|---|---|
| *D03D 1/00* | (2006.01) |
| *D04B 1/16* | (2006.01) |
| *G01K 3/06* | (2006.01) |
| *G01K 7/18* | (2006.01) |
| *G01K 13/20* | (2021.01) |
| *H05K 1/03* | (2006.01) |
| *A61B 5/00* | (2006.01) |
| *A61B 5/01* | (2006.01) |

(52) U.S. Cl.
CPC ........... *H05K 1/0393* (2013.01); *A41D 1/005* (2013.01); *A61B 5/015* (2013.01); *A61B 5/6804* (2013.01); *D03D 1/0088* (2013.01); *D04B 1/16* (2013.01); *G01K 7/04* (2013.01)

(58) Field of Classification Search
CPC ...... A41D 1/005; A61B 5/6804; A61B 5/015; A61B 2230/50; D03D 1/0088; D04B 1/12; D04B 1/16; D04B 2403/02431; H05K 1/038; H05K 1/0393
See application file for complete search history.

(56) References Cited

U.S. PATENT DOCUMENTS

| | | | | | |
|---|---|---|---|---|---|
| 4,659,873 | A | * | 4/1987 | Gibson ................. | H01H 3/141 |
| | | | | | 178/18.05 |
| 5,134,772 | A | | 8/1992 | McQueen | |
| 10,935,436 | B2 | * | 3/2021 | Sullivan .................... | G01K 7/04 |
| 11,313,734 | B2 | * | 4/2022 | Wen .......................... | D03D 1/00 |
| 11,353,366 | B2 | * | 6/2022 | Marchesi ........... | A41D 13/1281 |
| 11,891,733 | B2 | * | 2/2024 | Chahine .................... | A61B 5/01 |
| 2010/0245090 | A1 | * | 9/2010 | Smith .................. | H10N 10/854 |
| | | | | | 340/573.1 |
| 2011/0237001 | A1 | | 9/2011 | Hasebe et al. | |
| 2015/0023393 | A1 | * | 1/2015 | Britton ..................... | H01C 7/02 |
| | | | | | 374/185 |
| 2019/0017879 | A1 | * | 1/2019 | Sullivan .................... | G01K 7/04 |
| 2019/0353533 | A1 | | 11/2019 | Marchesi | |
| 2021/0048350 | A1 | * | 2/2021 | Damerow .............. | G01K 1/143 |
| 2021/0100460 | A1 | * | 4/2021 | Dagdeviren ........... | G01K 13/20 |
| 2025/0207981 | A1 | * | 6/2025 | Oakley .................... | D04B 1/16 |

OTHER PUBLICATIONS

Computer translation of KR_101518173 (Year: 2025).*
International Search Report and Written Opinion received in PCT/US2021/046818 mailed Nov. 8, 2021, 11 pages.
International Preliminary Report on Patentability issued for Application No. PCT/US2021/046818, dated Mar. 2, 2023.
Bai, Y. et al., 2018, "Flexible Heating Fabrics with Temperature Perception Based on Fine Copper Wire and Fusible Interlining Fabrics," Measurement, 122, pp. 192-200.
Chen, Y. et al., 2015, "Breathable and Stretchable Temperature Sensors Inspired by Skin," Sci. Rep., 5(1), p. 11505.
Dauphinee, T. M. et al., 1954, "A Copper Resistance Temperature Scale," Rev. Sci. Instrum., 25(9), pp. 884-886.
Fiala, D. et al., 1999, "A Computer Model of Human Thermoregulation for a Wide Range of Environmental Conditions: The Passive System," J. Appl. Physiol., 87(5), pp. 1957-1972.

Glycerine Producers' Assosiation, 1963, Physical Properties of Glycerine and its Solutions, Glycerine Producers' Association, New York.
Husain, M. D. et al., "Design and Fabrication of Temperature Sensing Fabric," Journal of Industrial Textiles, vol. 44, No. 3, pp. 398-417, 2014. http://journals.sagepub.com/doi/10.1177/1528083713495249.
Janicki, P. K. et al., 2002, "Water Warming Garment versus Forced Air Warming System in Prevention of Intraoperative Hypothermia during Liver Transplantation: A Randomized Controlled Trial [ISRCTN32154832]," BMC Anesthesiol., 2:7.
Jayathilaka, W. A. D. M. et al., 2019, "Significance of Nanomaterials in Wearables: A Review on Wearable Actuators and Sensors," Adv. Mater., 31(7), p. 1805921.
Khoshnevis, S. et al., 2014, "Quantitative Evaluation of the Thermal Heterogeneity on the Surface of Cryotherapy Cooling Pads," J. Biomech. Eng., 136(7), pp. 0745031-0745037.
Koo, T. K. et al., 2016, "A Guideline of Selecting and Reporting Intraclass Correlation Coefficients for Reliability Research," J. Chiropr. Med., 15(2), pp. 155-163.
Locher, I. et al., 2005, "Temperature Profile Estimation with Smart Textiles," In Proceedings of the International Conference on Intelligent Textiles, Smart Clothing, Well-Being, and Design.
Lugoda, P. et al., "Developing Novel Temperature Sensing Garments for Health Monitoring Applications," Fibers, vol. 6, No. 46, 2018. Available from: https://www.sciencedirect.com/science/article/pii/S0924424717302984.
Lugoda, P. et al., "Flexible Temperature Sensor Integration into E-Textiles Using Different Industrial Yarn Fabrication Processes," Sensors, vol. 20, No. 73, 2019.
Lugoda, P. et al., 2018, "A Wearable Textile Thermograph," Sensors, 18(7).
Mattana, G., et al., 2013, "Woven Temperature and Humidity Sensors on Flexible Plastic Substrates for E-Textile Applications," IEEE Sens. J., 13(10), pp. 3901-3909.
Monseau, A. J. et al., 2015, "Sunburn, Thermal, and Chemical Injuries to the Skin," Prim. Care Clin. Off. Pract., 42(4), pp. 591-605.
Nahabet, E. et al., 2017, "Contact Cooling of Random-Pattern Cutaneous Flaps: Does It Increase Necrosis?," Aesthetic Plast. Surg., 41(2), pp. 448-453.
Namisnak, L. H. et al., 2019, "Selective Thermal Stimulation Delays the Progression of Vasoconstriction During Body Cooling," J. Biomech. Eng., 141(12), pp. 124504-1-6.
National Electrical Manufacturers Association, 2016, "NEMA MW 1000—Magnet Wire."
Oğlakcioğlu, N. et al., 2007, "Thermal Comfort Properties of Some Knitted Structures," Fibres Text. East. Eur., (Nr 5-6 (64)), pp. 94-96.
Park, S., Chung, K., & Jayaraman, S. (2014). Wearables. Wearable Sensors, 1- 23. doi: 10.1016/b978-0-12-418662-0.00001-5.
Polansky, R. et al., "A Novel Large-area Embroidered Temperature Sensor Based on an Innovative Hybrid Resistive Thread," Sensors and Actuators A: Physical, vol. 265, pp. 111-119, 2017.
Romanovsky, A. A., 2018, "Chapter 1—The Thermoregulation System and How It Works," Handbook of Clinical Neurology, A.A. Romanovsky, ed., Elsevier, pp. 3-43.
Shih, W.-P. et al., 2010, "Flexible Temperature Sensor Array Based on a Graphite-Polydimethylsiloxane Composite," Sensors, 10(4), pp. 3597-3610.
Shin, J. et al., 2020, "Sensitive Wearable Temperature Sensor with Seamless Monolithic Integration," Adv. Mater., 32(2), p. 1905527.
Stoll, A. M. et al., 1950, "Study of Thermocouples as Skin Thermometers," J. Appl. Physiol., 2(10), pp. 531-543.
Truell, K. D. et al., 2000, "Third-Degree Burns Due to Intraoperative Use of a Bair Hugger Warming Device," Ann. Thorac. Surg., 69(6), pp. 1933-1934.
United States. National Bureau of Standards and Institute for Applied Technology (U.S.), Office of Engineering Standards, 1966, Copper Wire Tables, National Bureau of Standards.
Varon, J. et al., 2008, "Therapeutic Hypothermia," Chest, 133(5), pp. 1267-1274.

(56) References Cited

OTHER PUBLICATIONS

Wu, R. et al., 2019, "Silk Composite Electronic Textile Sensor for High Space Precision 2D Combo Temperature-Pressure Sensing," Small, 15(31), p. 1901558.

Yang, J. et al., 2015, "Wearable Temperature Sensor Based on Graphene Nanowalls," RSC Adv., 5(32), pp. 25609-25615.

Yang, Y.-J. et al., 2008, "An Integrated Flexible Temperature and Tactile Sensing Array Using PI-Copper Films," Sens. Actuators Phys., 143(1), pp. 143-153.

Zak, R. B. et al., 2018, "Impact of Local Heating and Cooling on Skeletal Muscle Transcriptional Response Related to Myogenesis and Proteolysis," Eur. J. Appl. Physiol., 118(1), pp. 101-109.

* cited by examiner

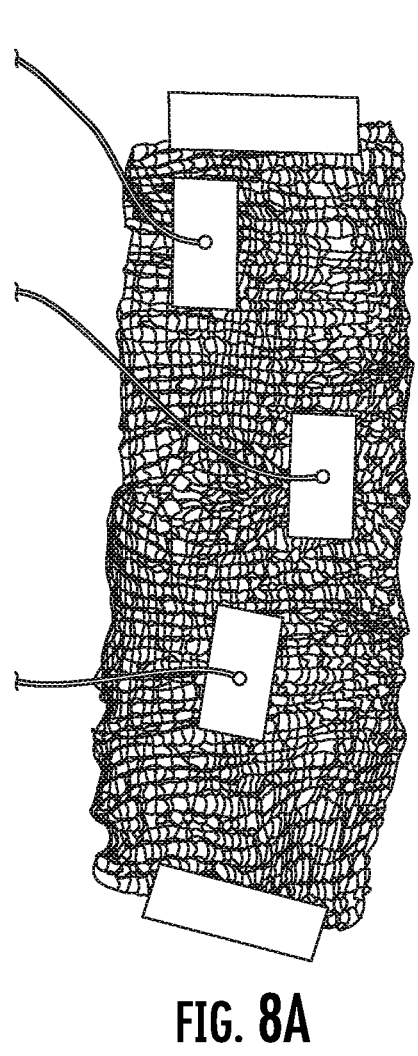
FIG. 8A
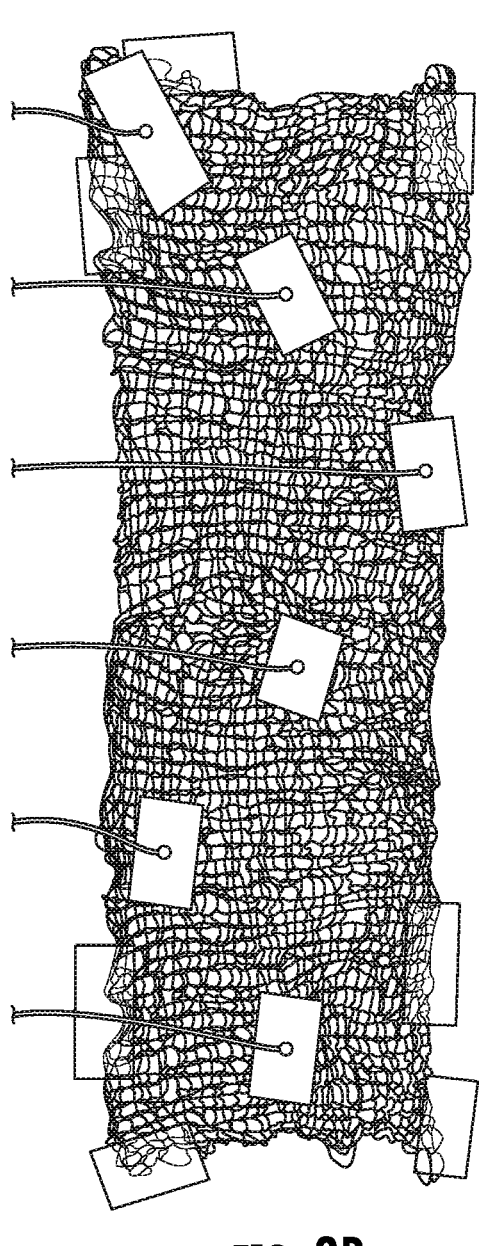
FIG. 8B

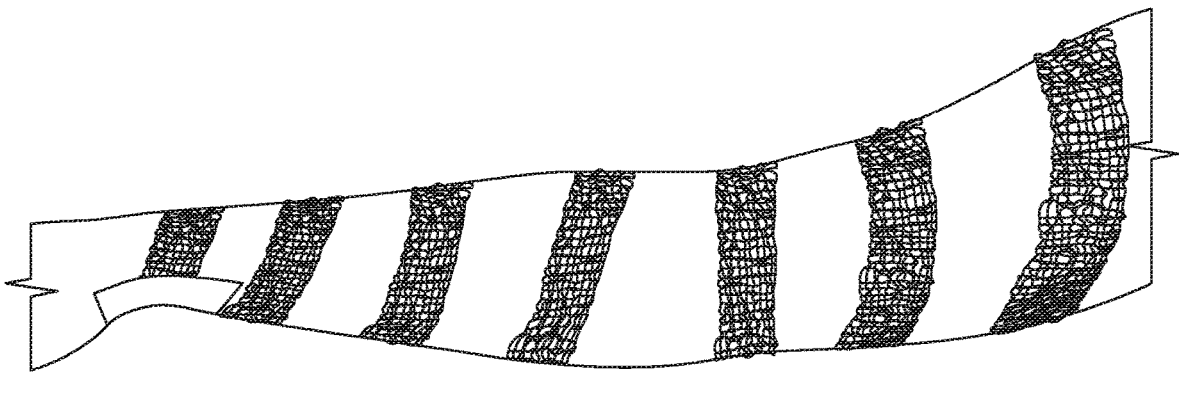
FIG. 20A
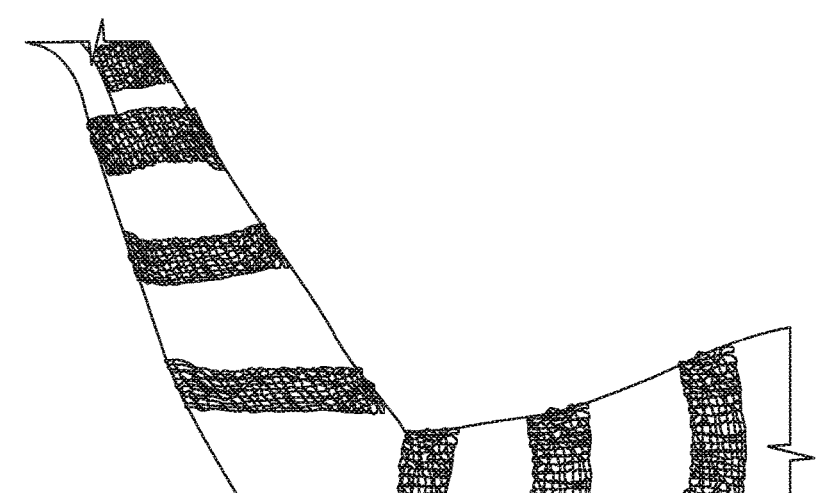
FIG. 20B

TWO-DIMENSIONAL RESISTANCE TEMPERATURE DETECTORS AND RELATED METHODS FOR DETERMINING AVERAGE TEMPERATURE OVER A SURFACE

CROSS-REFERENCE TO RELATED APPLICATIONS

This application is a U.S. National Stage application filed under 35 U.S.C. § 371 of PCT/US2021/046818 filed Aug. 20, 2021, which claims priority to and the benefit of U.S. Provisional Application No. 63/068,776, filed Aug. 21, 2020, the disclosure of which is expressly incorporated by reference in its entirety.

GOVERNMENT SUPPORT CLAUSE

This invention was made with government support under Grant no. R42 GM119871 awarded by the National Institutes of Health. The government has certain rights in the invention.

FIELD OF THE DISCLOSURE

The present disclosure relates generally to temperature sensors and more particularly to two-dimensional resistance temperature detectors and related methods of using the same for determining average temperature over a surface via direct contact.

BACKGROUND OF THE DISCLOSURE

Various types of devices may be used for measuring or otherwise determining surface temperature of an object or a living subject. For example, surface-temperature measurements often may be obtained via direct contact with a surface of interest using traditional point sensors, such as thermocouples, thermistors, or resistance temperature detectors (RTDs). Although these types of contact temperature sensors have been ubiquitous for temperature monitoring throughout industry and academia for more than a century, they typically provide a temperature value at only a single point. Accordingly, measurements obtained using such sensors may be accurate for surface temperature only if temperature is spatially uniform over the surface of interest. In many thermal applications, surface temperature may be nonuniform, and thus traditional contact temperature sensors may not be suitable for such applications. For instance, certain heat transfer processes may produce lateral variations in surface temperature that have a significant effect on a process outcome, resulting in a need to monitor temperature over an area (i.e., via two-dimensional (2D) sensing) rather than just a single point.

One method commonly used for 2D thermal sensing is infrared thermography, which involves optically interrogating, instead of directly contacting, a surface. In some applications, however, direct optical access to a target surface may not be feasible. For example, in certain applications involving thermoregulation of a human subject, it may be necessary to monitor mean skin temperature over a large surface that is at least partially covered by clothing. As another example, in other applications, a water-perfused garment may be placed on a human subject's skin to manipulate core temperature for therapeutic benefit, with the garment at least partially covering a target surface. In these applications, infrared thermography may not be suitable for measuring surface temperature due to an inability to directly view a target surface. Infrared thermography also may have limitations in measuring surface temperature over a target surface having a complex-shaped geometry. In particular, when using infrared thermography, curvature of a target surface may introduce measurement errors due to geometric shape factor effects on the distance and the viewing angle between the surface and a camera detector.

In recent years, several designs have been proposed for incorporating a temperature sensor into a textile structure to measure temperature of a human subject for health monitoring applications or other purposes. In some instances, such designs may be provided as wearable sensors. According to one design, a metal sensing wire is embedded within a knitted textile substrate in a serpentine fashion to form a temperature sensing fabric. See Husain, M. D. et al., "Design and Fabrication of Temperature Sensing Fabric," *Journal of Industrial Textiles*, vol. 44, no. 3, pp. 398-417, 2014. Another design involves embroidering a hybrid resistive thread having polyester fibers and a metal microwire onto a carrier fabric to provide an embroidered temperature sensor. See Polansky, R. et al., "A Novel Large-area Embroidered Temperature Sensor Based on an Innovative Hybrid Resistive Thread," *Sensors and Actuators A: Physical*, vol. 265, pp. 111-119, 2017. According to another design, a temperature sensing garment includes embedded textile-based temperature sensors having thermistors that are soldered to metal wires, encapsulated in a polymer resin, and covered with packing fibers and a knitted tube to form a temperature sensing yarn. See Lugoda, P. et al., "Developing Novel Temperature Sensing Garments for Health Monitoring Applications," *Fibers*, vol. 6, no. 46, 2018. Yet another design involves embedding flexible RTDs within the fibers of a textile yarn to provide a flexible temperature sensor. See Lugoda, P. et al., "Flexible Temperature Sensor Integration into E-Textiles Using Different Industrial Yarn Fabrication Processes," *Sensors*, vol. 20, no. 73, 2019. Although these textile-based temperature sensing devices may be useful in some applications, they may present certain limitations. For example, the textile structure may prevent or minimize direct contact between the wires or sensing structure and a surface of interest, resulting in inaccurate temperature measurements. Additionally, the textile structure may limit flexibility of the overall device and the ability of the wires or sensing structure to conform to the shape of a target surface.

A need therefore exists for improved devices and methods for determining surface temperature, such as average surface temperature, of an object or a living subject, which may overcome one or more of the above-mentioned problems associated with existing and proposed temperature sensing technology.

SUMMARY OF THE DISCLOSURE

The present disclosure provides two-dimensional resistance temperature detectors and related methods of using the same for determining average temperature over a surface via direct contact. In one aspect, a two-dimensional resistance temperature detector for determining average temperature over a surface is provided. In one embodiment, the two-dimensional resistance temperature detector may include a continuous length of insulated wire having a first end and a second end. The insulated wire may be arranged to form a mesh structure with respective sections of the insulated wire overlapping and contacting one another.

In some embodiments, the insulated wire may include a metal wire and a coating disposed over the metal wire. In some embodiments, the metal wire may be a magnet wire. In some embodiments, the metal wire may include copper. In some embodiments, the metal wire may include aluminum. In some embodiments, the coating may be an enamel coating. In some embodiments, the coating may include a polymer. In some embodiments, the coating may include polymer film electrical insulation. In some embodiments, the insulated wire may be arranged in a knitted pattern to form the mesh structure. In some embodiments, the insulated wire may be arranged in a woven pattern to form the mesh structure. In some embodiments, the insulated wire may be arranged in a crocheted pattern to form the mesh structure.

In some embodiments, the two-dimensional resistance temperature detector may have a first side and a second side disposed opposite the first side, and the mesh structure may define a plurality of openings extending from the first side to the second side between adjacent sections of the insulated wire. In some embodiments, a maximum thickness of the two-dimensional resistance temperature detector between the first side and the second may be equal to twice a thickness of the insulated wire. In some embodiments, the insulated wire may include a plurality of overlapping sections each having a first thickness and a plurality of non-overlapping sections each having a second thickness that is greater than the first thickness, and a maximum thickness of the two-dimensional resistance temperature detector between the first side and the second side may be less than twice the second thickness. In some embodiments, a thickness of the insulated wire between the first side and the second side may be less than a width of the insulated wire along at least a portion of the insulated wire. In some embodiments, the openings each may have a width that is greater than a thickness of the insulated wire and a length that is greater than the thickness of the insulated wire. In some embodiments, the two-dimensional resistance temperature detector may be devoid of material within the openings. In some embodiments, the two-dimensional resistance temperature detector may be configured for positioning over the surface such that one of the first side or the second side directly contacts the surface. In some embodiments, the two-dimensional resistance temperature detector may be configured for positioning over the surface such that the insulated wire directly contacts the surface. In some embodiments, the two-dimensional resistance temperature detector may be configured for positioning over the surface such that a majority of a length of the insulated wire directly contacts the surface. In some embodiments, the mesh structure may be flexible such that the mesh structure is configured for conforming to a shape of the surface. In some embodiments, the two-dimensional resistance temperature detector may be devoid of any fabric material.

In another aspect, a method for determining average temperature over a surface is provided. In one embodiment, the method may include positioning a two-dimensional resistance temperature detector over the surface such that an insulated wire of the two-dimensional resistance temperature detector directly contacts the surface, determining a resistance of the insulated wire, and determining an average surface temperature based at least in part on the resistance of the insulated wire. The insulated wire may be arranged to form a mesh structure with respective sections of the insulated wire overlapping and contacting one another.

In some embodiments, the insulated wire may include a metal wire and a coating disposed over the metal wire. In some embodiments, the metal wire may be a magnet wire. In some embodiments, the metal wire may include copper. In some embodiments, the metal wire may include aluminum. In some embodiments, the coating may be an enamel coating. In some embodiments, the coating may include a polymer. In some embodiments, the coating may include polymer film electrical insulation. In some embodiments, the insulated wire may be arranged in a knitted pattern to form the mesh structure. In some embodiments, the insulated wire may be arranged in a woven pattern to form the mesh structure. In some embodiments, the insulated wire may be arranged in a crocheted pattern to form the mesh structure.

In some embodiments, the two-dimensional resistance temperature detector may have a first side and a second side disposed opposite the first side, and the mesh structure may define a plurality of openings extending from the first side to the second side between adjacent sections of the insulated wire. In some embodiments, a maximum thickness of the two-dimensional resistance temperature detector between the first side and the second may be equal to twice a thickness of the insulated wire. In some embodiments, the insulated wire may include a plurality of overlapping sections each having a first thickness and a plurality of non-overlapping sections each having a second thickness that is greater than the first thickness, and a maximum thickness of the two-dimensional resistance temperature detector between the first side and the second side may be less than twice the second thickness. In some embodiments, a thickness of the insulated wire between the first side and the second side may be less than a width of the insulated wire along at least a portion of the insulated wire. In some embodiments, the openings each may have a width that is greater than a thickness of the insulated wire and a length that is greater than the thickness of the insulated wire. In some embodiments, the two-dimensional resistance temperature detector may be devoid of material within the openings. In some embodiments, positioning the two-dimensional resistance temperature detector over the surface may include positioning the two-dimensional resistance temperature detector over the surface such that one of the first side or the second side directly contacts the surface. In some embodiments, positioning the two-dimensional resistance temperature detector over the surface may include positioning the two-dimensional resistance temperature detector over the surface such that a majority of a length of the insulated wire directly contacts the surface. In some embodiments, positioning the two-dimensional resistance temperature detector over the surface may include conforming the mesh structure to a shape of the surface. In some embodiments, the two-dimensional resistance temperature detector may be devoid of any fabric material. In some embodiments, the surface may be a contoured surface. In some embodiments, the surface may be an external surface of an object. In some embodiments, the surface may be an external surface of a living subject.

In some embodiments, the method also may include positioning a heating device or a cooling device over the surface, and causing a temperature setting of the heating device or the cooling device to change based at least in part on the average surface temperature. In some embodiments, positioning the heating device or the cooling device over the surface may include positioning the heating device or the cooling device such that the heating device or the cooling device directly contacts the surface. In some embodiments, positioning the heating device or the cooling device over the surface may include positioning the heating device or the cooling device such that the heating device or the cooling device directly contacts the two-dimensional resistance temperature detector. In some embodiments, positioning the heating device or the cooling device over the surface may include positioning the heating device or the cooling device such that at least a portion of the two-dimensional resistance temperature detector is positioned between the surface and the heating device or the cooling device. In some embodiments, the surface may be an internal surface of a heating device or a cooling device. In some embodiments, the method also may include causing a temperature setting of the heating device or the cooling device to change based at least in part on the average surface temperature. In some embodiments, the surface may be at least partially covered by an object, and positioning the two-dimensional resistance temperature detector over the surface may include positioning the two-dimensional resistance temperature detector between the surface and the object. In some embodiments, the surface may be an interface between two or more objects.

In still another aspect, a two-dimensional resistance temperature detector for determining average temperature over a surface is provided. In one embodiment, the two-dimensional resistance temperature detector may include a plurality of insulated wires each having a first end and a second end. The insulated wires may be arranged to form a mesh structure with respective sections of each of the insulated wires overlapping and contacting one another.

In some embodiments, each of the insulated wires may include a metal wire and a coating disposed over the metal wire. In some embodiments, the metal wire may be a magnet wire. In some embodiments, the metal wire may include copper. In some embodiments, the metal wire may include aluminum. In some embodiments, the coating may be an enamel coating. In some embodiments, the coating may include a polymer. In some embodiments, the coating may include polymer film electrical insulation. In some embodiments, the insulated wires may be arranged in a knitted pattern to form the mesh structure. In some embodiments, the insulated wires may be arranged in a woven pattern to form the mesh structure. In some embodiments, the insulated wires may be arranged in a crocheted pattern to form the mesh structure.

In some embodiments, the two-dimensional resistance temperature detector may have a first side and a second side disposed opposite the first side, and the mesh structure may define a plurality of openings extending from the first side to the second side between adjacent sections of the insulated wires. In some embodiments, a maximum thickness of the two-dimensional resistance temperature detector between the first side and the second may be equal to twice a thickness of the insulated wires. In some embodiments, each of the insulated wires may include a plurality of overlapping sections each having a first thickness and a plurality of non-overlapping sections each having a second thickness that is greater than the first thickness, and a maximum thickness of the two-dimensional resistance temperature detector between the first side and the second side may be less than twice the second thickness. In some embodiments, for each of the insulated wires, a thickness of the insulated wire between the first side and the second side may be less than a width of the insulated wire along at least a portion of the insulated wire. In some embodiments, the openings each may have a width that is greater than a thickness of each of the insulated wires and a length that is greater than the thickness of each of the insulated wires. In some embodiments, the two-dimensional resistance temperature detector may be devoid of material within the openings. In some embodiments, the two-dimensional resistance temperature detector may be configured for positioning over the surface such that one of the first side or the second side directly contacts the surface. In some embodiments, the two-dimensional resistance temperature detector may be configured for positioning over the surface such that each of the insulated wires directly contacts the surface. In some embodiments, the two-dimensional resistance temperature detector may be configured for positioning over the surface such that a majority of a length of each of the insulated wires directly contacts the surface. In some embodiments, the mesh structure may be flexible such that the mesh structure is configured for conforming to a shape of the surface. In some embodiments, the two-dimensional resistance temperature detector may be devoid of any fabric material.

In yet another aspect, a method for determining average temperature over a surface is provided. In one embodiment, the method may include positioning a two-dimensional resistance temperature detector over the surface such that each of a plurality of insulated wires of the two-dimensional resistance temperature detector directly contacts the surface, determining resistances of the insulated wires, and determining an average surface temperature based at least in part on the resistances of the insulated wires. The insulated wires may be arranged to form a mesh structure with respective sections of each of the insulated wires overlapping and contacting one another.

In some embodiments, each of the insulated wires may include a metal wire and a coating disposed over the metal wire. In some embodiments, the metal wire may be a magnet wire. In some embodiments, the metal wire may include copper. In some embodiments, the metal wire may include aluminum. In some embodiments, the coating may be an enamel coating. In some embodiments, the coating may include a polymer. In some embodiments, the coating may include polymer film electrical insulation. In some embodiments, the insulated wires may be arranged in a knitted pattern to form the mesh structure. In some embodiments, the insulated wires may be arranged in a woven pattern to form the mesh structure. In some embodiments, the insulated wires may be arranged in a crocheted pattern to form the mesh structure.

In some embodiments, the two-dimensional resistance temperature detector may have a first side and a second side disposed opposite the first side, and the mesh structure may define a plurality of openings extending from the first side to the second side between adjacent sections of the insulated wires. In some embodiments, a maximum thickness of the two-dimensional resistance temperature detector between the first side and the second may be equal to twice a thickness of the insulated wires. In some embodiments, each of the insulated wires may include a plurality of overlapping sections each having a first thickness and a plurality of non-overlapping sections each having a second thickness that is greater than the first thickness, and a maximum thickness of the two-dimensional resistance temperature detector between the first side and the second side may be less than twice the second thickness. In some embodiments, for each of the insulated wires, a thickness of the insulated wire between the first side and the second side may be less than a width of the insulated wire along at least a portion of the insulated wire. In some embodiments, the openings each may have a width that is greater than a thickness of each of the insulated wires and a length that is greater than the thickness of each of the insulated wires. In some embodiments, the two-dimensional resistance temperature detector may be devoid of material within the openings. In some embodiments, positioning the two-dimensional resistance temperature detector over the surface may include positioning the two-dimensional resistance temperature detector over the surface such that one of the first side or the second side directly contacts the surface. In some embodiments, positioning the two-dimensional resistance temperature detector over the surface may include positioning the two-dimensional resistance temperature detector over the surface such that a majority of a length of each of the insulated wires directly contacts the surface. In some embodiments, positioning the two-dimensional resistance temperature detector over the surface may include conforming the mesh structure to a shape of the surface. In some embodiments, the two-dimensional resistance temperature detector may be devoid of any fabric material. In some embodiments, the surface may be a contoured surface. In some embodiments, the surface may be an external surface of an object. In some embodiments, the surface may be an external surface of a living subject.

In some embodiments, the method also may include positioning a heating device or a cooling device over the surface, and causing a temperature setting of the heating device or the cooling device to change based at least in part on the average surface temperature. In some embodiments, positioning the heating device or the cooling device over the surface may include positioning the heating device or the cooling device such that the heating device or the cooling device directly contacts the surface. In some embodiments, positioning the heating device or the cooling device over the surface may include positioning the heating device or the cooling device such that the heating device or the cooling device directly contacts the two-dimensional resistance temperature detector. In some embodiments, positioning the heating device or the cooling device over the surface may include positioning the heating device or the cooling device such that at least a portion of the two-dimensional resistance temperature detector is positioned between the surface and the heating device or the cooling device. In some embodiments, the surface may be an internal surface of a heating device or a cooling device. In some embodiments, the method also may include causing a temperature setting of the heating device or the cooling device to change based at least in part on the average surface temperature. In some embodiments, the surface may be at least partially covered by an object, and positioning the two-dimensional resistance temperature detector over the surface may include positioning the two-dimensional resistance temperature detector between the surface and the object. an invisible surface. In some embodiments, the surface may be an interface between two or more objects.

In another aspect, a two-dimensional resistance temperature detector for determining average temperature over a surface is provided. In one embodiment, the two-dimensional resistance temperature detector may include a plurality of insulated wires arranged to form a plurality of regions of the two-dimensional resistance temperature detector. Each of the insulated wires may have a first end and a second end and may be arranged to form a mesh structure of a respective region of the plurality of regions. The two-dimensional resistance temperature detector may have a first side and a second side disposed opposite the first side, and the regions may not overlap one another in a direction from the first side to the second side.

In some embodiments, each of the insulated wires may include a metal wire and a coating disposed over the metal wire. In some embodiments, the metal wire may be a magnet wire. In some embodiments, the metal wire may include copper. In some embodiments, the metal wire may include aluminum. In some embodiments, the coating may be an enamel coating. In some embodiments, the coating may include a polymer. In some embodiments, the coating may include polymer film electrical insulation. In some embodiments, each of the insulated wires may be arranged in a knitted pattern to form the mesh structure of the respective region. In some embodiments, each of the insulated wires may be arranged in a woven pattern to form the mesh structure of the respective region. In some embodiments, each of the insulated wires may be arranged in a crocheted pattern to form the mesh structure of the respective region.

In some embodiments, each of the mesh structures may define a plurality of openings extending from the first side to the second side between adjacent sections of the respective insulated wire. In some embodiments, a maximum thickness of the two-dimensional resistance temperature detector between the first side and the second may be equal to twice a thickness of each of the insulated wires. In some embodiments, each of the insulated wires may include a plurality of overlapping sections each having a first thickness and a plurality of non-overlapping sections each having a second thickness that is greater than the first thickness, and a maximum thickness of the two-dimensional resistance temperature detector between the first side and the second side may be less than twice the second thickness. In some embodiments, for each of the insulated wires, a thickness of the insulated wire between the first side and the second side may be less than a width of the insulated wire along at least a portion of the insulated wire. In some embodiments, the openings each may have a width that is greater than a thickness of each of the insulated wires and a length that is greater than the thickness of each of the insulated wires. In some embodiments, the two-dimensional resistance temperature detector may be devoid of material within the openings. In some embodiments, the two-dimensional resistance temperature detector may be configured for positioning over the surface such that one of the first side or the second side directly contacts the surface. In some embodiments, the two-dimensional resistance temperature detector may be configured for positioning over the surface such that each of the insulated wires directly contacts the surface. In some embodiments, the two-dimensional resistance temperature detector may be configured for positioning over the surface such that a majority of a length of each of the insulated wires directly contacts the surface. In some embodiments, each of the mesh structures may be flexible such that the mesh structures are configured for conforming to a shape of the surface. In some embodiments, the two-dimensional resistance temperature detector may be devoid of any fabric material. In some embodiments, the plurality of regions may include at least four regions. In some embodiments, the plurality of regions may be arranged in an array. In some embodiments, adjacent pairs of the regions may abut one another along respective edges thereof. In some embodiments, the two-dimensional resistance temperature detector may be configured for determining average temperatures for respective regions of the surface, and the regions of the two-dimensional resistance temperature detector may correspond to the respective regions of the surface. In some embodiments, the two-dimensional resistance temperature detector may be configured for determining an average temperature for the surface based at least in part on the average temperatures for the respective regions of the surface.

In still another aspect, a method for determining average temperature over a surface is provided. In one embodiment, the method may include positioning a two-dimensional resistance temperature detector over the surface such that each of a plurality of insulated wires of the two-dimensional resistance temperature detector directly contacts the surface, determining resistances of the insulated wires, and determining, based at least in part on the resistances of the insulated wires, average surface temperatures for respective surface regions of the surface, wherein the regions of the two-dimensional resistance temperature detector correspond to the respective surface regions of the surface. The insulated wires may be arranged to form a plurality of regions of the two-dimensional resistance temperature detector. Each of the insulated wires may be arranged to form a mesh structure of a respective region of the plurality of regions. The two-dimensional resistance temperature detector may have a first side and a second side disposed opposite the first side, and the regions may not overlap one another in a direction from the first side to the second side.

In some embodiments, each of the insulated wires may include a metal wire and a coating disposed over the metal wire. In some embodiments, the metal wire may be a magnet wire. In some embodiments, the metal wire may include copper. In some embodiments, the metal wire may include aluminum. In some embodiments, the coating may be an enamel coating. In some embodiments, the coating may include a polymer. In some embodiments, the coating may include polymer film electrical insulation. In some embodiments, each of the insulated wires may be arranged in a knitted pattern to form the mesh structure of the respective region. In some embodiments, each of the insulated wires may be arranged in a woven pattern to form the mesh structure of the respective region. In some embodiments, each of the insulated wires may be arranged in a crocheted pattern to form the mesh structure of the respective region.

In some embodiments, each of the mesh structures may define a plurality of openings extending from the first side to the second side between adjacent sections of the respective insulated wire. In some embodiments, a maximum thickness of the two-dimensional resistance temperature detector between the first side and the second may be equal to twice a thickness of each of the insulated wires. In some embodiments, each of the insulated wires may include a plurality of overlapping sections each having a first thickness and a plurality of non-overlapping sections each having a second thickness that is greater than the first thickness, and a maximum thickness of the two-dimensional resistance temperature detector between the first side and the second side may be less than twice the second thickness. In some embodiments, for each of the insulated wires, a thickness of the insulated wire between the first side and the second side may be less than a width of the insulated wire along at least a portion of the insulated wire. In some embodiments, the openings each may have a width that is greater than a thickness of each of the insulated wires and a length that is greater than the thickness of each of the insulated wires. In some embodiments, the two-dimensional resistance temperature detector may be devoid of material within the openings. In some embodiments, positioning the two-dimensional resistance temperature detector over the surface may include positioning the two-dimensional resistance temperature detector over the surface such that one of the first side or the second side directly contacts the surface. In some embodiments, positioning the two-dimensional resistance temperature detector over the surface may include positioning the two-dimensional resistance temperature detector over the surface such that a majority of a length of each of the insulated wires directly contacts the surface. In some embodiments, positioning the two-dimensional resistance temperature detector over the surface may include conforming the mesh structures to a shape of the surface. In some embodiments, the two-dimensional resistance temperature detector may be devoid of any fabric material. In some embodiments, the surface may be a contoured surface. In some embodiments, the surface may be an external surface of an object. In some embodiments, the surface may be an external surface of a living subject.

In some embodiments, the method also may include positioning a heating device or a cooling device over the surface, and causing a temperature setting of the heating device or the cooling device to change based at least in part on one or more of the average surface temperatures. In some embodiments, wherein positioning the heating device or the cooling device over the surface may include positioning the heating device or the cooling device such that the heating device or the cooling device directly contacts the surface. In some embodiments, positioning the heating device or the cooling device over the surface may include positioning the heating device or the cooling device such that the heating device or the cooling device directly contacts the two-dimensional resistance temperature detector. In some embodiments, positioning the heating device or the cooling device over the surface may include positioning the heating device or the cooling device such that at least a portion of the two-dimensional resistance temperature detector is positioned between the surface and the heating device or the cooling device. In some embodiments, the surface may be an internal surface of a heating device or a cooling device. In some embodiments, the method also may include causing a temperature setting of the heating device or the cooling device to change based at least in part on one or more of the average surface temperatures. In some embodiments, the surface may be at least partially covered by an object, and positioning the two-dimensional resistance temperature detector over the surface may include positioning the two-dimensional resistance temperature detector between the surface and the object. In some embodiments, the surface may be an interface between two or more objects. In some embodiments, the plurality of regions may include at least four regions. In some embodiments, the plurality of regions may be arranged in an array. In some embodiments, adjacent pairs of the regions may abut one another along respective edges thereof. In some embodiments, the method also may include determining, based at least in part on the average surface temperatures for respective surface regions of the surface, an average surface temperature for the entire surface.

These and other aspects and improvements of the present disclosure will become apparent to one of ordinary skill in the art upon review of the following detailed description when taken in conjunction with the several drawings and the appended claims.

BRIEF DESCRIPTION OF THE DRAWINGS

FIG. 8A is a top view of an experimental setup of an example first two-dimensional resistance temperature detector in accordance with one or more embodiments of the disclosure and a plurality of thermocouples. FIG. 8B is a top view of an experimental setup of an example second two-dimensional resistance temperature detector in accordance with one or more embodiments of the disclosure and a plurality of thermocouples.

FIG. 20A is a photograph of an example two-dimensional resistance temperature detector wrapped around a human arm, showing the arm in an extended position. FIG. 20B is a photograph of the two-dimensional resistance temperature detector of FIG. 20A wrapped around the arm, showing the arm in a flexed position.

Figure 1:
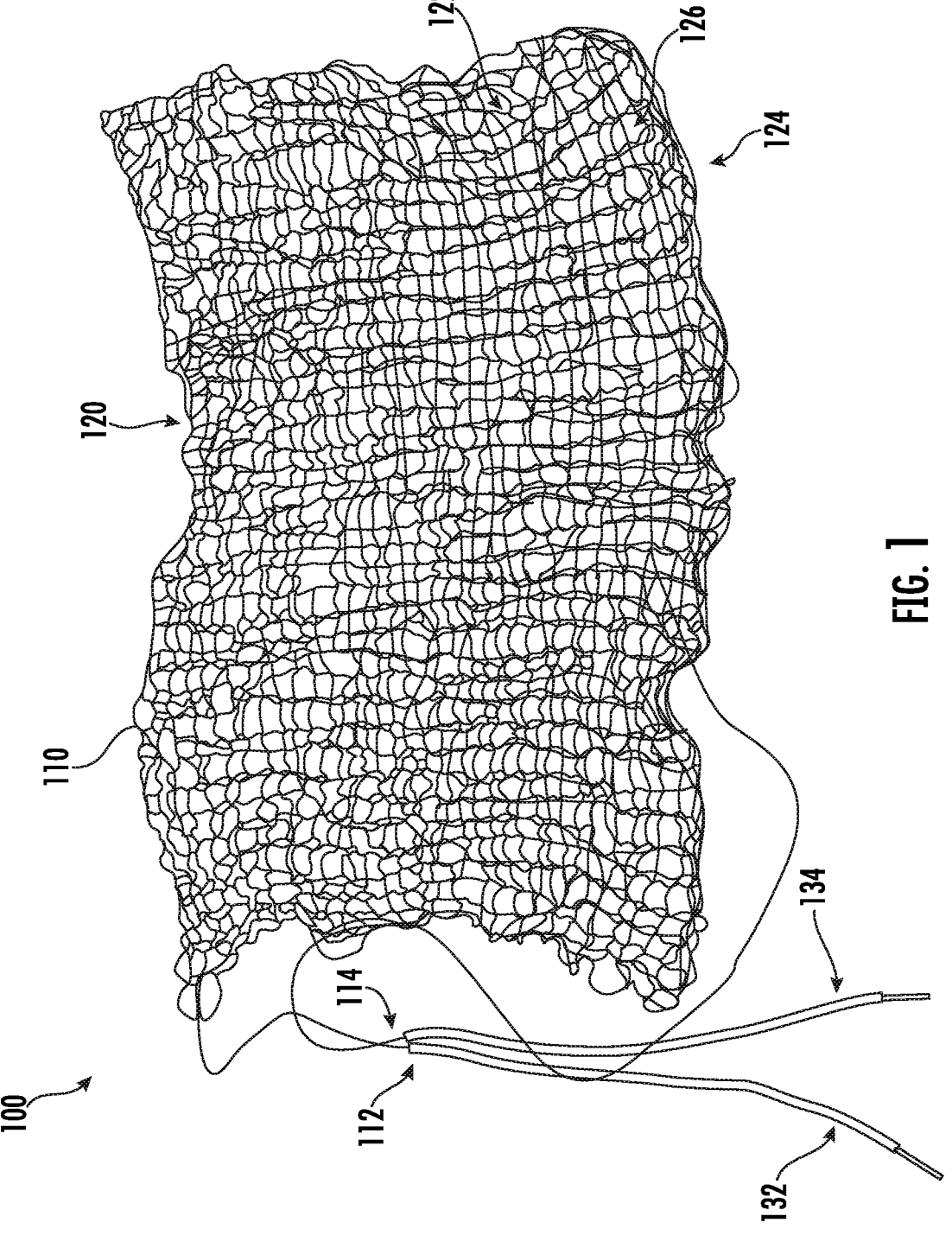
FIG. 1 is a top view of an example two-dimensional resistance temperature detector in accordance with one or more embodiments of the disclosure.

The detailed description is set forth with reference to the accompanying drawings. The drawings are provided for purposes of illustration only and merely depict example embodiments of the disclosure. The drawings are provided to facilitate understanding of the disclosure and shall not be deemed to limit the breadth, scope, or applicability of the disclosure. The use of the same reference numerals indicates similar, but not necessarily the same or identical components. Different reference numerals may be used to identify similar components. Various embodiments may utilize elements or components other than those illustrated in the drawings, and some elements and/or components may not be present in various embodiments. The use of singular terminology to describe a component or element may, depending on the context, encompass a plural number of such components or elements and vice versa.

DETAILED DESCRIPTION OF THE DISCLOSURE

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional. In some instances, well known methods, procedures, and components have not been described in detail so as not to unnecessarily obscure aspects of the embodiments.

Overview

Embodiments of two-dimensional resistance temperature detectors and related methods of using the same for determining average temperature over a surface are provided herein. The two-dimensional resistance temperature detectors and methods may be used to determine surface temperature, such as average surface temperature, of an object or a living subject via direct contact. In some embodiments, a two-dimensional resistance temperature detector generally may include a continuous length of insulated wire having a first end and a second end, with the insulated wire being arranged to form a mesh structure with respective sections of the insulated wire overlapping and contacting one another. In other embodiments, a two-dimensional resistance temperature detector generally may include a plurality of insulated wires each having a first end and a second end, with the insulated wires being arranged to form a mesh structure with respective sections of each of the insulated wires overlapping and contacting one another.

As discussed above, existing and proposed temperature sensing technology may have limitations with respect to certain applications. Although traditional contact temperature sensors may be useful for determining a temperature value at a single point, such sensors generally may not be suitable for accurately determining surface temperature, particularly when temperature is not spatially uniform over a surface of interest. As an alternative, infrared thermography may be used as an effective technique for assessing the pattern and magnitude of a two-dimensional temperature field by optically interrogating a surface of interest. However, the use of infrared thermography may not be feasible in certain applications, for example, when the surface of interest is at least partially covered and not optically accessible. Additionally, infrared thermography may present limitations in measuring surface temperature when the surface of interest has a complex-shaped geometry, resulting in measurement errors due to geometric shape factor effects on the distance and the viewing angle between the surface and a camera detector. Proposed textile-based temperature sensing devices also may have limitations due to the configuration of the textile structure used in such devices. In some instances, the textile structure may prevent or minimize direct contact between the wires or sensing structure and a surface of interest, resulting in inaccurate temperature measurements. Additionally, the textile structure may limit flexibility of the overall device and the ability of the wires or sensing structure to conform to the shape of a target surface.

The two-dimensional resistance temperature detectors and methods described herein advantageously may overcome one or more of the limitations associated with existing and proposed temperature sensing technology. As compared to conventional contact temperature sensors, the two-dimensional resistance temperature detectors may be used to accurately determine surface temperature, such as average surface temperature, in applications in which temperature is spatially nonuniform over a surface of interest. The two-dimensional resistance temperature detectors provided herein also may be useful in applications in which the use of infrared thermography is not be feasible, such as when a surface of interest is not optically accessible. Additionally, as compared to infrared thermography, the two-dimensional resistance temperature detectors may be used to more accurately determine surface temperature in applications in which a surface of interest has a complex-shaped geometry. The two-dimensional resistance temperature detectors provided herein also may provide advantages over textile-based temperature sensing devices. In particular, by not including a textile structure, the two-dimensional resistance temperature detectors may maximize direct contact between the insulated wire(s) and a surface of interest and also may provide greater flexibility for allowing the mesh structure to conform to the shape of the surface, resulting in more accurate determinations of surface temperature.

Although the two-dimensional resistance temperature detectors and methods provided herein may be used in various applications, they may be particularly beneficial for use in applications involving thermoregulation of a human subject. Specifically, the two-dimensional resistance temperature detectors may be used to accurately monitor average skin temperature over an external surface of the subject's body, even when significant lateral variations in temperature exist over the surface. Skin temperature and its local variation over the body surface are important inputs to the human thermoregulatory system. In many experimental studies of thermoregulation, temperature may be manipulated independently as a governing variable by having a subject wear a full-body water-perfused garment consisting of a mesh of polymer tubes woven into a fabric suit that extends to the neck, wrists, and ankles of the subject. Typically, the spacing between adjacent tubes is on the order of 3-6 cm, giving rise to lateral temperature differences as large as several degrees Celsius. The human body effectively integrates these surface temperature variations into an input signal to its central controller. Analyzing and modeling the role of skin temperature based on experimental data requires measurement of the inputs to the controller. Advantageously, the two-dimensional resistance temperature detectors provided herein may be used to accurately monitor average skin temperature via direct contact with the subject's body. In particular, one or more of the two-dimensional resistance temperature detectors may be placed over and in contact with a surface of interest, between the subject's body and a water-perfused garment. In this manner, the two-dimensional resistance temperature detectors may provide a direct-contact solution in instances in which infrared thermography cannot be used. Furthermore, the highly-flexible nature of the mesh structure allows the two-dimensional resistance temperature detectors to readily conform to the surface of any human anatomical shape.

Thermoregulation research and various medical procedures may be accomplished by manipulating skin temperature in a nonuniform pattern. In some instances, skin temperature monitoring may be essential to assess conformance to protocol specifications and to prevent thermal injury. As discussed above, existing solutions for skin temperature monitoring include single point sensors, such as thermocouples, and two-dimensional methods of sensing surface temperature, such as infrared thermography, and wearable technology. Single point sensors cannot detect the average temperature and consequently their measurements cannot be representative of average surface temperature in a nonuniform temperature field. Infrared thermography requires optical access, and existing ambulatory sensors may require complex manufacturing processes and impede the heat exchange with a source by including a structural substrate layer. As described herein, the disclosed two-dimensional resistance temperature detectors and methods advantageously may address these problems with existing technology.

The function of the human thermoregulatory system operates with a key input being the skin temperature averaged over extended areas of the body surface. See Romanovsky, A. A., 2018, "Chapter 1—The Thermoregulation System and How It Works," *Handbook of Clinical Neurology*, A. A. Romanovsky, ed., Elsevier, pp. 3-43. The measurement of this property is impossible using point sensors, as skin temperature is inherently nonuniform for many reasons including distance from heat generating organs, insulation provided by clothing, and nonuniform environmental conditions. The body uses an integrated skin temperature as an input to the thermoregulatory control center, and for studies in thermoregulation, a sensor that does the same is necessary.

In addition to thermoregulation research, mean skin temperature measurement may be important in specific clinical settings. For example, skin temperature manipulation may be required during cryotherapy, thermotherapy, therapeutic hypothermia, maintaining perioperative normothermia, and other thermally based medical procedures. Modalities for manipulation often are based on means of heat exchange that produce a nonuniform temperature pattern across the surface of the skin. Each of these treatments frequently may be achieved by a recirculating water bath connected to a water perfused pad, blanket, or garment that is in direct thermal communication with the skin surface. See Zak, R. B. et al., 2018, "Impact of Local Heating and Cooling on Skeletal Muscle Transcriptional Response Related to Myogenesis and Proteolysis," *Eur. J. Appl. Physiol.*, 118(1), pp. 101-109; Nahabet, E. et al., 2017, "Contact Cooling of Random-Pattern Cutaneous Flaps: Does It Increase Necrosis?," *Aesthetic Plast. Surg.*, 41(2), pp. 448-453; Varon, J. et al., 2008, "Therapeutic Hypothermia," *Chest,* 133(5), pp. 1267-1274; Janicki, P. K. et al., 2002, "Water Warming Garment versus Forced Air Warming System in Prevention of Intraoperative Hypothermia during Liver Transplantation: A Randomized Controlled Trial IISRCTN321548321," *BMC Anesthesiol.,* 2, p. 7. To maximize surface area contact, the front of the pad may be welded to the back of the pad to create discrete channels through which water flows. These welds may interrupt the thermal continuity on the face of the pad that contacts the skin, thus creating nonuniform skin temperature. See Khoshnevis, S. et al., 2014, "Quantitative Evaluation of the Thermal Heterogeneity on the Surface of Cryotherapy Cooling Pads," *J. Biomech. Eng.,* 136(7), pp. 0745031-0745037. Therapeutic hypothermia and perioperative normothermia can also be achieved by a convective air blanket. See Varon, J. et al.; Janicki, P. K. et al. Cooled or heated air may flow through the blanket interior and exit through small holes on the surface adjacent to the skin. Placement of the outlet holes may create a nonuniform pattern of cooling or heating on the skin and a heterogenous temperature distribution. See Truell, K. D. et al., 2000, "Third-Degree Burns Due to Intraoperative Use of a Bair Hugger Warming Device," *Ann. Thorac. Surg.,* 69(6), pp. 1933-1934. It generally may be important to have an accurate measure of skin temperature to ensure proper operation of the skin temperature manipulation modality and to avoid thermal injury, such as nonfreezing cold injury and burn. See Monseau, A. J. et al., 2015, "Sunburn, Thermal, and Chemical Injuries to the Skin," *Prim. Care Clin. Off. Pract.,* 42(4), pp. 591-605.

Single point thermocouples have been used to measure skin temperature during exposure to a uniform boundary condition. See Stoll, A. M. et al., 1950, "Study of Thermocouples as Skin Thermometers," *J. Appl. Physiol.,* 2(10), pp. 531-543. However, single point temperature sensors will not represent the average temperature of a nonuniform surface. A two-dimensional temperature sensor that can conform to the complex skin surface morphology is required to accurately measure average skin temperature that is a result of a nonuniform boundary condition as occurs, for example, when wearing a water-perfused garment.

Prior to the use of thermocouples, radiometers were adapted to monitor skin temperature. See Stoll, A. M. et al. Radiometers require optical access to the skin surface, as do modern infrared (IR) imagers. Optical access may not available when the skin is covered during contact temperature manipulation. In the past decade, there have been interests and advancements in wearable technology. See Jayathilaka, W. A. D. M. et al., 2019, "Significance of Nanomaterials in Wearables: A Review on Wearable Actuators and Sensors," *Adv. Mater.,* 31(7), p. 1805921. Wearables are ambulatory sensing devices placed on the body and used to collect data for both personal and medical purposes. See Park, S. et al., 2021, "Chapter 1—Wearables: Fundamentals, Advancements, and a Roadmap for the Future," *Wearable Sensors (Second Edition)*, E. Sazonov, ed., Academic Press, Oxford, pp. 3-27. There are two common methods for creating a temperature sensing wearable. The first incorporates a thermal sensor(s) into a wearable substrate material and may or may not involve a complicated manufacturing process. See Yang, Y.-J. et al., 2008, "An Integrated Flexible Temperature and Tactile Sensing Array Using PI-Copper Films," *Sens. Actuators Phys.,* 143(1), pp. 143-153; Shih, W.-P. et al., 2010, "Flexible Temperature Sensor Array Based on a Graphite-Polydimethylsiloxane Composite," *Sensors,* 10(4), pp. 3597-3610; Locher, I. et al., 2005, "Temperature Profile Estimation with Smart Textiles," *In Proceedings of the International Conference on Intelligent Textiles, Smart Clothing, Well-Being, and Design*; Chen, Y. et al., 2015, "Breathable and Stretchable Temperature Sensors Inspired by Skin," *Sci. Rep.,* 5(1), p. 11505; Mattana, G., et al., 2013, "Woven Temperature and Humidity Sensors on Flexible Plastic Substrates for E-Textile Applications," *IEEE Sens. J.,* 13(10), pp. 3901-3909; Husain, M. D. et al., 2014, "Design and Fabrication of Temperature Sensing Fabric," J. Ind. Text., 44(3), pp. 398-417; Bai, Y. et al., 2018, "Flexible Heating Fabrics with Temperature Perception Based on Fine Copper Wire and Fusible Interlining Fabrics," *Measurement,* 122, pp. 192-200; Yang, J. et al., 2015, "Wearable Temperature Sensor Based on Graphene Nanowalls," *RSC Adv.,* 5(32), pp. 25609-25615; Shin, J. et al., 2020, "Sensitive Wearable Temperature Sensor with Seamless Monolithic Integration," *Adv. Mater.,* 32(2), p. 1905527. This method creates an added layer of thermal insulation impeding the heat transfer between the source and the skin. The second method is to create a temperature sensing yarn by spinning temperature sensing fibers integrated with textile fibers then weaving the yarn into a substrate fabric or manufacturing a new fabric. See Lugoda, P. et al., 2018, "A Wearable Textile Thermograph," Sensors, 18(7); Wu, R. et al., 2019, "Silk Composite Electronic Textile Sensor for High Space Precision 2D Combo Temperature-Pressure Sensing," *Small,* 15(31), p. 1901558. This option requires an arduous manufacturing process.

The two-dimensional resistance temperature detectors provided herein may be easily manufactured with inexpensive, readily available materials. In some embodiments, copper wire may be used as a temperature sensitive conductor due to its stable and reproduceable resistance-temperature characteristics. See Dauphinee, T. M. et al., 1954, "A Copper Resistance Temperature Scale," *Rev. Sci. Instrum.,* 25(9), pp. 884-886. The operating principle of such two-dimensional resistance temperature detectors is based on the fact that the electrical resistance of the copper wire changes with temperature in a fully predictable manner Therefore, the wire can be used as a transducer to sense temperature when properly calibrated. Although other wire materials may be used in other embodiments, copper magnet wire may be well suited for the two-dimensional resistance temperature detectors because it is easy to procure, inexpensive, and electrically insulated. As described below, the copper wire may be used as the "yarn" for manufacturing the two-dimensional resistance temperature detectors by knitting, either by hand or using industrial knitting machines, although weaving or crocheting techniques may be used in other embodiments. The final shape of the two-dimensional resistance temperature detectors may be readily customizable, allowing fabrication to be tailored for various applications.

As discussed below, example two-dimensional resistance temperature detectors were fabricated, calibrated, compared to one-dimensional sensors and wearable sensors, and analyzed for hysteresis, repeatability, and surface area conformation. Resistance and temperature were correlated with an $R^2$ of 0.99. In summary, the two-dimensional resistance temperature detectors were shown to be a superior device for measuring average skin temperature over a defined area exposed to a nonuniform temperature boundary in the absence of optical access, such as when a full body thermal control garment is worn.

Still other benefits and advantages of the two-dimensional resistance temperature detectors and methods provided herein over existing and proposed temperature sensing technology will be appreciated by those of ordinary skill in the art from the following description and the appended drawings.

Two-Dimensional Resistance Temperature Detectors

Referring now to FIG. 1, an example two-dimensional resistance temperature detector 100 (which also may be referred to as a "2D RTD," a "resistance temperature detector," an "RTD," a "contact temperature sensor," a "temperature sensor," or simply a "sensor") is depicted. The resistance temperature detector 100 is configured for determining surface temperature, such as average surface temperature, of an object or a living subject via direct contact with the surface of interest. In some embodiments, the resistance temperature detector 100 may be used to determine and monitor average skin temperature of a human subject in thermoregulatory applications, although various other uses of the resistance temperature detector 100 may be envisioned by those of ordinary skill in the art.

As shown in FIG. 1, the resistance temperature detector 100 may include a continuous length of insulated wire 110 having a first end 112 and a second end 114. The insulated wire 110 may be arranged to form a mesh structure 120 with respective sections of the insulating wire 110 overlapping and contacting one another. In other words, the mesh structure 120 may be formed entirely by the single insulated wire 110, as shown in FIG. 1. In some embodiments, the insulated wire 110 may be arranged in a knitted pattern, according to one or more knitting techniques, to form the mesh structure 120. In some embodiments, the insulated wire 110 may be arranged in a woven pattern, according to one or more weaving techniques, to form the mesh structure 120. In some embodiments, the insulated wire 110 may be arranged in a crocheted pattern, according to one or more crocheting techniques, to form the mesh structure 120. Still other patterns of arranging the insulated wire 110 to form the mesh structure 120 may be used in other embodiments. In some embodiments, the mesh structure 120 may have a generally rectangular shape, as shown in FIG. 1. Various other shapes of the mesh structure 120, including regular and irregular shapes, may be used in other embodiments, with the shape and size of the mesh structure 120 being selected to accommodate a particular surface of interest.

The insulated wire 110 may include a metal wire and a coating disposed over the metal wire. The metal wire may include or may be formed of any metal suitable for use as a thermal sensor. In some embodiments, the metal wire may include or may be formed of copper. In some embodiments, the metal wire may include or may be formed of aluminum. Still other suitable metals may be used for the metal wire in other embodiments. In some embodiments, the metal wire may be a magnet wire of the type typically used for the core windings of electric motors. The coating may include or may be formed of any material suitable for electrically insulating the metal wire. In some embodiments, the coating may include or may be formed of a polymer. Still other suitable materials may be used for the coating in other embodiments. In some embodiments, the coating may include or may be formed of polymer film electrical insulation. The coating may surround the metal wire and may extend from the first end 112 to the second end 114 of the insulated wire 110. The insulated wire 110 may be highly flexible such that the insulated wire 110 and the overall mesh structure 120 formed thereby may be deformed to readily conform to a shape of a surface of interest. The mechanical properties of the insulated wire 110 may enable the wire 110 to be deformed with a small radius of curvature without fracture or interrupting the continuity of the insulating coating. Various wire gauges may be used for the insulated wire 110 to modulate the total electrical resistance and mechanical flexibility and resilience for different embodiments of the resistance temperature detector 100. In some embodiments, the insulated wire 110 may have a circular cross-sectional shape, although other cross-sectional shapes of the wire 110 may be used in other embodiments. The insulated wire 110 may have a thickness (i.e., diameter when the wire 110 has a circular cross-sectional shape) that is constant or substantially constant along the length of the wire 110.

The resistance temperature detector 100 may have a first side 122 (which also may be referred to as a "top side") and a second side 124 (which also may be referred to as a "bottom side") disposed opposite one another. In some embodiments, a maximum thickness of the resistance temperature detector 100 between the first side 122 and the second side 124 may be equal to twice the thickness of the insulated wire 110. For example, the maximum thickness of the resistance temperature detector 100 may correspond to a region of the mesh structure 120 where one section of the insulated wire 110 overlaps another section of the insulated sire 110. In some embodiments, the insulated wire 110 may include a plurality of overlapping sections each having a first thickness and a plurality of non-overlapping sections each having a second thickness that is different from the first thickness. In some embodiments, the second thickness may be greater than the first thickness, and the maximum thickness of the two-dimensional resistance temperature detector 100 between the first side 122 and the second side 124 may be less than twice the second thickness. Such a relationship may be achieved by flattening some or all of the insulated wire 110 after arranging the insulated wire 110 to form the mesh structure 120. In some embodiments, flattening of some or all of the insulated wire 110 may be achieved by applying one or more rollers to the mesh structure 120, by pressing the mesh structure 120 between a pair of plates, or by other means for mechanically flattening the insulated wire 110. In some embodiments, only the overlapping sections of the insulated wire 110 may be flattened to a reduced thickness, while the non-overlapping sections of the insulated wire 110 maintain their original thickness. In some embodiments, the overlapping sections and the non-overlapping sections of the insulated wire 110 each may be flattened to respective reduced thicknesses, with the non-overlapping sections being flattened to a lesser degree. In some embodiments, along at least a portion of the insulated wire 110, a thickness of the insulated wire 110 between the first side 122 and the second side 124 may be less than a width of the insulated wire 110 (i.e., the width dimension in a direction perpendicular to the thickness dimension between the first side 122 and the second side 124). As shown in FIG. 1, the mesh structure 120 may define a plurality of openings 126 extending from the first side 122 to the second side 124 and between adjacent sections of the insulated wire 110. Various shapes of the openings 126 may be used, as may result from the pattern used to arrange the insulated wire 110 to form the mesh structure 120. The openings 126 each may have a width dimension and a length dimension. In some embodiments, as shown, the openings 126 each may have a width that is greater than the thickness of the insulated wire 110 and a length that is greater than the thickness of the insulated wire 110. In this manner, the dimensions of the openings relative to the thickness of the insulated wire 110 may enhance the flexibility of the overall mesh structure 120, allowing the mesh structure 120 to readily conform to a shape of a surface of interest. As shown, the resistance temperature detector 100 may be devoid of material within the openings 126. In this manner, the resistance temperature detector 100 may provide greater flexibility than textile-based temperature sensing devices having textile material disposed around and/or between wires or sensing elements.

The resistance temperature detector 100 may be configured such that one of the first side 122 and the second side 124 may be positioned over and in contact with a surface of interest during use of the resistance temperature detector 100. In other words, the resistance temperature detector 100 may be configured for positioning over the surface of interest such that one of the first side 122 or the second side 124 directly contacts the surface. As shown, the insulated wire 110 may be exposed along each of the first side 122 and the second side 124. Accordingly, the resistance temperature detector 100 may be configured for positioning over the surface of interest such that the insulated wire 110 directly contacts the surface. In some embodiments, as shown, the resistance temperature detector 100 may be configured for positioning over the surface of interest such that a majority of the length of the insulated wire 110 directly contacts the surface. As mentioned above, the mesh structure 120 may be flexible such that the mesh structure 120 is configured for conforming to a shape of the surface of interest. In some embodiments, as shown, the resistance temperature detector 100 may be devoid of any fabric material. As shown in FIG. 1, the resistance temperature detector 100 may be formed entirely by the insulated wire 110, without any additional materials, such as fabric materials, that would reduce flexibility of the resistance temperature detector 100.

In some embodiments, the resistance temperature detector 100 may include a pair of lead wires coupled to the respective ends of the insulated wire 110. For example, the resistance temperature detector 100 may include a first lead wire 132 coupled to the first end 112 of the insulated wire 110 and a second lead wire 134 coupled to the second end 114 of the insulated wire 110. The lead wires 132, 134 may be configured for connecting to a resistance module during use of the resistance temperature detector 100.

In various applications, the resistance temperature detector 100 may be used for determining average temperature over a surface of interest. The resistance temperature detector 100 may be positioned over the surface of interest such that the insulated wire 110 directly contacts the surface. In particular, the resistance temperature detector 100 may be positioned over the surface of interest such that respective portions of the insulated wire 110 along the first side 122 or the second side 124 of the resistance temperature detector 100 directly contact the surface. In some embodiments, a majority of the length of the insulated wire 110 may directly contact the surface of interest. In some embodiments, the mesh structure 120 may conform to a shape of the surface of interest due to the flexibility of the insulated wire 110 and the overall mesh structure 120. After positioning the resistance temperature detector 100, a resistance of the insulated wire 110 may be determined. For example, a resistance module connected to the resistance temperature detector 100 may be used to acquire resistance data for the resistance temperature detector 100 and determine the resistance of the insulated wire 110. Then, an average surface temperature of the surface of interest may be determined based at least in part on the resistance of the insulated wire 110. For example, as described below, a resistance-temperature relationship for the resistance temperature detector 100 may be used to determine the average surface temperature based at least in part on the resistance of the insulated wire 110.

Although the above-described embodiments may be provided with a single insulated wire 110, alternative embodiments of the resistance temperature detector 100 may include a plurality of insulated wires 110 that are arranged to form the mesh structure 120 with respective sections of each of the insulated wires 110 overlapping and contacting one another. For example, the resistance temperature detector 100 may include two (2), three (3), four (4), or more of the insulated wires 110 arranged to form the mesh structure 120. Various arrangements of the insulated wires 110 may be used. According to different embodiments, resistances of the insulated wires 110 may be determined in series or in parallel, and an average surface temperature of a surface of interest may be determined based at least in part on the resistances of the insulated wires 110. In some instances, the use of more than one insulated wire 110 may improve accuracy of the resistance temperature detector 100 and/or may improve robustness of the resistance temperature detector 100 (e.g., if one of the insulated wires 110 is cut off).

Figure 2:
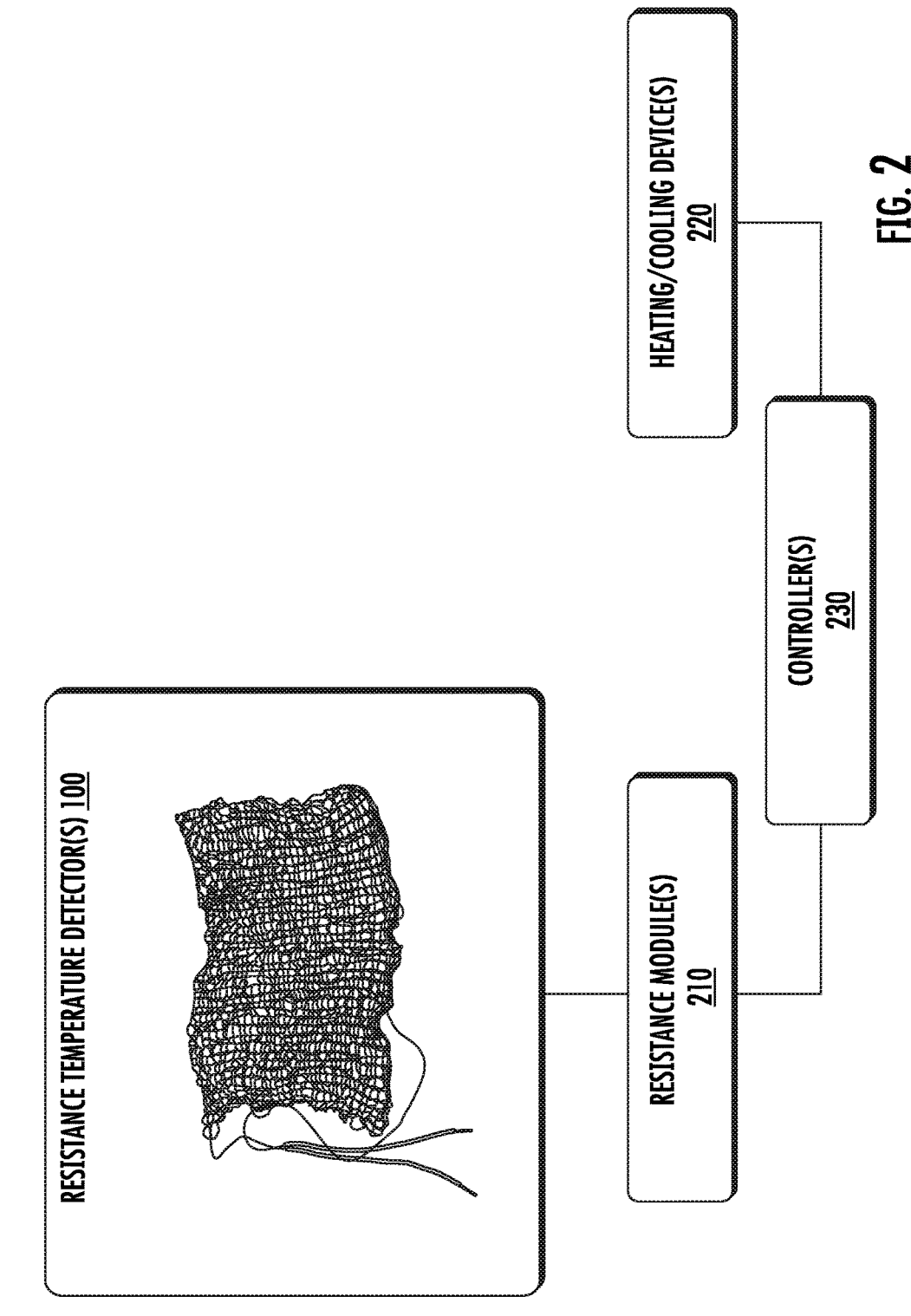
FIG. 2 is a schematic illustration of a system in accordance with one or more embodiments of the disclosure, the system including at least one resistance temperature detector, at least one resistance module, at least one heating or cooling device, and at least one controller.

As shown in FIG. 2, one or more of the resistance temperature detectors 100 may be used as a part of a system 200 in certain applications. In addition to the resistance temperature detector(s) 100, the system 200 may include one or more resistance module(s) 210, one or more heating or cooling device(s) 220, and one or more controller(s) 230. The resistance module(s) 210 may be in operable communication with the resistance temperature detector(s) 100 for acquiring resistance data therefrom. The resistance module(s) 210 may be configured to determine a resistance value of the insulated wire(s) 110 of each of the resistance temperature detector(s) 100 during use thereof. The controller(s) 230 may be in operable communication with the resistance module(s) 210 and configured to receive the resistance values therefrom. The heating or cooling device(s) 220 may be configured to heat and/or cool a surface of interest, depending on the particular application. The controller(s) 230 may be in operable communication with the heating or cooling device(s) 220 and configured to adjust a temperature setting of the heating or cooling device(s) 220.

In some embodiments, the system 200 may provide real-time feedback control for regulating a temperature of a surface of interest. As described above, the resistance temperature detector(s) 100 may be positioned over the surface of interest, with the mesh structure 120 directly contacting the surface. The heating or cooling device(s) 220 may be positioned over the surface of interest for heating and/or cooling the surface. In some embodiments, the heating or cooling device(s) 220 may be positioned such that at least a portion of the resistance temperature detector(s) 100 is positioned between the surface of interest and the heating or cooling device(s) 220. In some embodiments, at least a portion of the heating or cooling device(s) 220 may directly contact the surface of interest. For example, respective portions of the heating or cooling device(s) 220 may directly contact the surface of interest through the openings 126 of the resistance temperature detector(s) 100. In some embodiments, the heating or cooling device(s) 220 may be positioned such that at least a portion of the heating or cooling device(s) 220 directly contacts the resistance temperature detector(s) 100. During use of the system 200, the controller(s) 230 may receive one or more resistance value(s) from the resistance module(s) 210 and then determine an average surface temperature over the surface of interest based at least in part on the resistance value(s). For example, the controller(s) 230 may determine the average surface temperature based on the resistance value(s) and a resistance-temperature relationship for the resistance temperature detector(s) 100. Then, the controller(s) 230 may cause one or more temperature setting(s) of the heating or cooling device(s) 220 to change based at least in part on the average surface temperature. For example, the controller(s) 230 may compare the average surface temperature to a target temperature and then cause the temperature setting(s) of the heating or cooling device(s) 220 to be increased or decreased based on a difference between the average surface temperature and the target temperature. Such feedback control may be performed continuously or periodically over a period of time to regulate the temperature of the surface of interest.

In some embodiments, the surface of interest may be a contoured surface. In some embodiments, the surface of interest may be an external surface of an object. In some embodiments, the surface of interest may not be an externally visible surface. In other words, the surface of interest may be at least partially covered by an object. In some embodiments, the surface of interest may be an interface between two or more objects. In some embodiments, the surface of interest may be an external surface of a living subject, such as a human subject. For example, the system 200 may be used for monitoring and controlling average skin temperature of a human subject in thermoregulation applications. Various other potential uses and applications of the system 200 will be appreciated by those of ordinary skill in the art.

Figure 3:
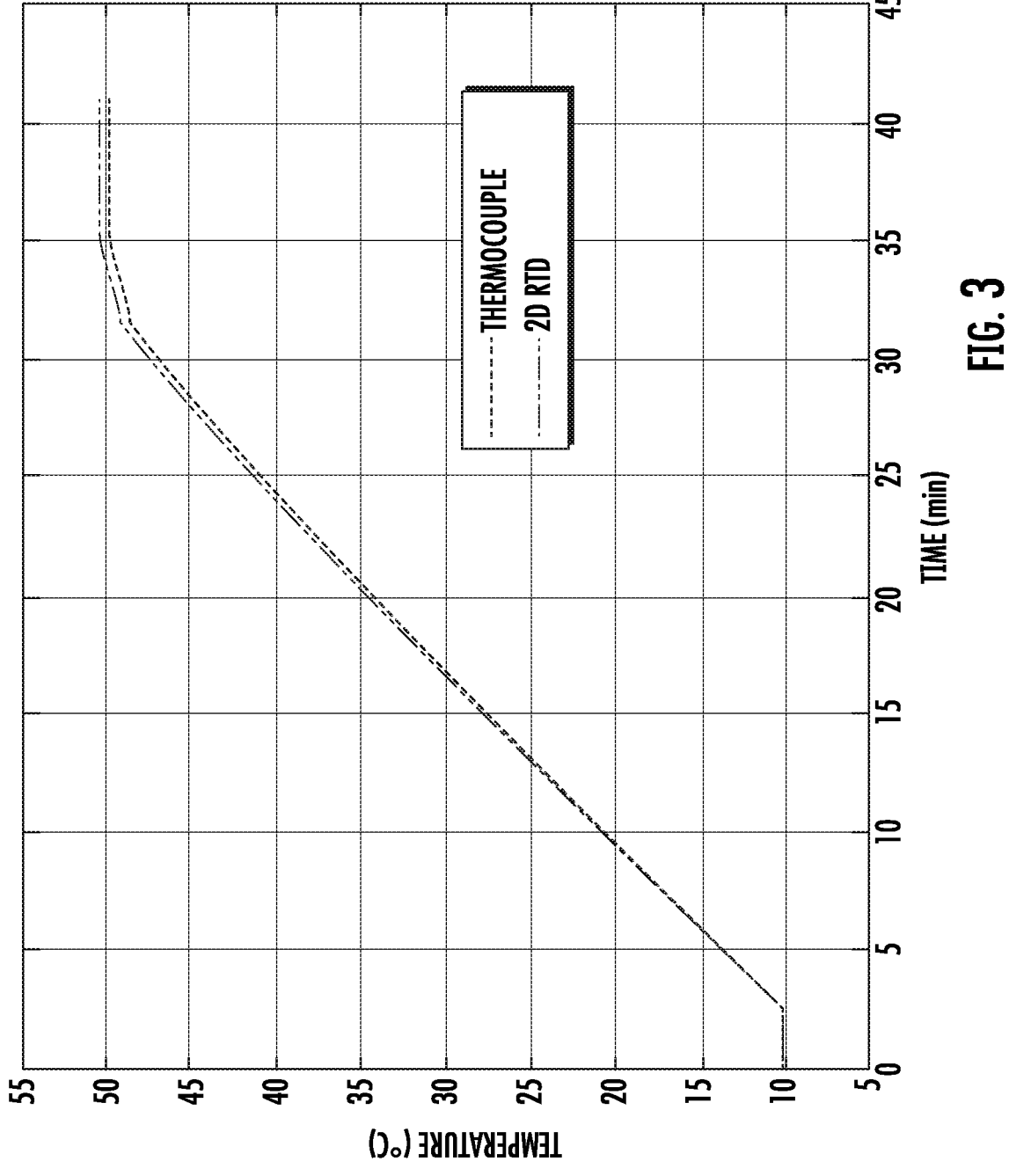
FIG. 3 is a graph of temperature as a function of time, illustrating an example validation of temperature measurement using a two-dimensional resistance temperature detector in accordance with one or more embodiments of the disclosure.

As discussed above, average surface temperature of a surface of interest may be determined based on the resistance of the insulated wire 110 and a resistance-temperature relationship for the resistance temperature detector 100. In particular, the following equation may be used for the resistance-temperature relationship:

$$R(T) = R_{ref}(1 + \alpha(T - T_{ref}))$$

where $R_{ref}$ is the resistance of the material of the metal wire at a reference temperature $T_{ref}$, and a is the temperature coefficient of resistance for the metal wire. A single point calibration may be performed for the resistance temperature detector 100 by evaluating $R_{ref}$ at $T_{ref} = 20°$ C., although any reference point may be used. The applicability of the above equation for the resistance temperature detector 100 was validated by calibrating the resistance temperature detector 100 in a water bath at different temperatures in the range of 10-50° C. The temperature as determined using the resistance temperature detector 100 closely followed the water bath temperature as monitored independently by thermocouples. FIG. 3 illustrates data from an example calibration validation experiment in which the behavior was highly linear and accurate.

Figure 4:
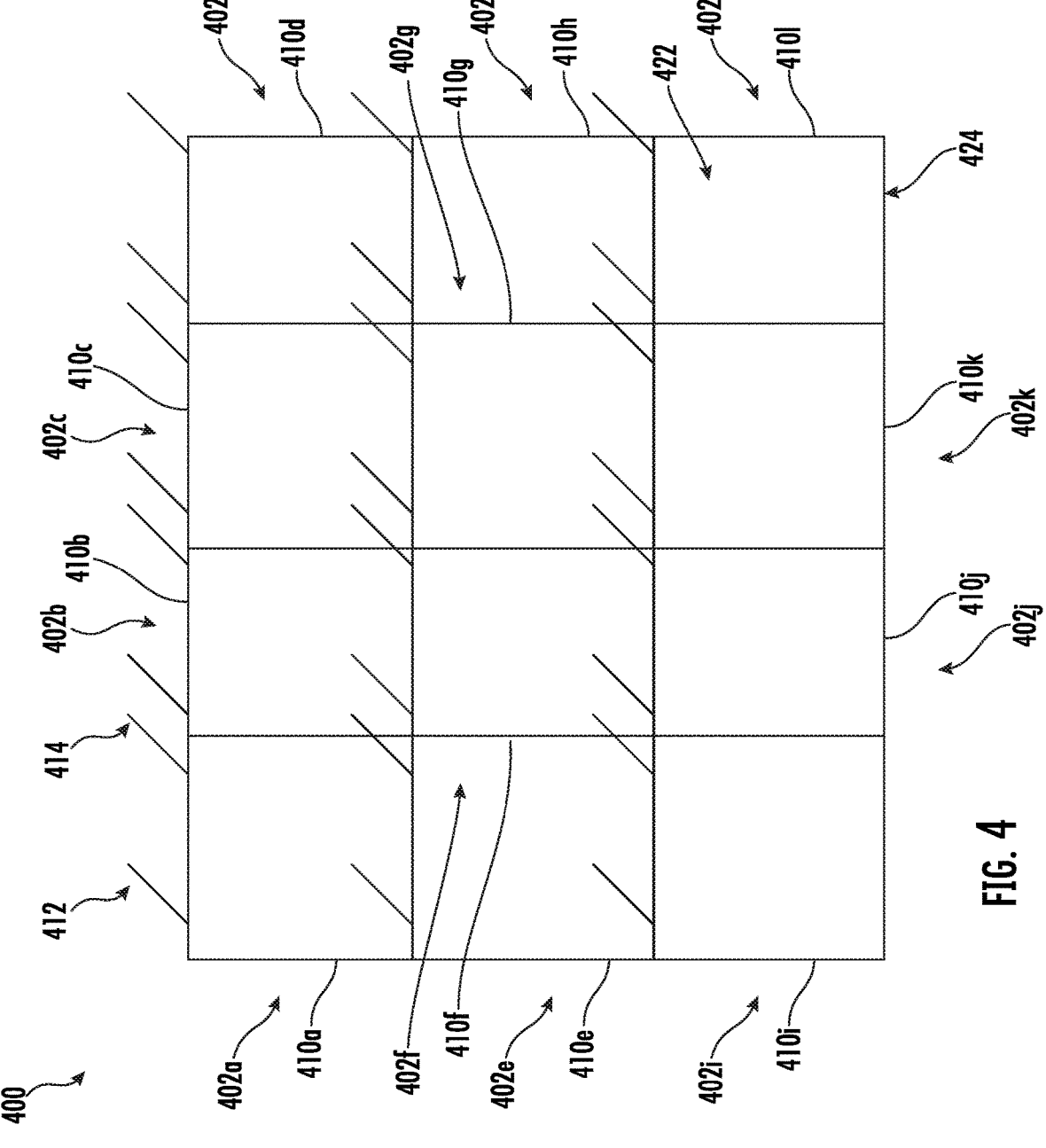
FIG. 4 is a schematic illustration of an example two-dimensional resistance temperature detector in accordance with one or more embodiments of the disclosure.

FIG. 4 schematically depicts another example two-dimensional resistance temperature detector 400 (which also may be referred to as a "2D RTD," a "resistance temperature detector," an "RTD," a "contact temperature sensor," a "temperature sensor," or simply a "sensor"). The resistance temperature detector 400 is configured for determining surface temperature, such as average surface temperature, of an object or a living subject via direct contact with the surface of interest. In some embodiments, the resistance temperature detector 400 may be used to determine and monitor average skin temperature of a human subject in thermoregulatory applications, although various other uses of the resistance temperature detector 400 may be envisioned by those of ordinary skill in the art. Certain similarities and differences between the resistance temperature detector 400 and the resistance temperature detector 100 will be appreciated from the drawings and the description provided herein. A particular difference relates to the resistance temperature detector 400 including a plurality of insulated wires configured for determining surface temperature of respective regions of a surface of interest.

As shown in FIG. 4, the resistance temperature detector 400 may include a plurality of regions 402 each configured for determining surface temperature, such as average surface temperature, of a respective region of a surface of interest. In this manner, the resistance temperature detector 400 may be used to determine respective average surface temperatures of different regions of the surface of interest. Further, as described below, the resistance temperature detector 400 may be used to determine overall average surface temperature of the entire surface of interest. As shown, the resistance temperature detector 400 may include a first region 402a, a second region 402b, a third region 402c, a fourth region 402d, a fifth region 402e, a sixth region 402f, a seventh region 402g, an eighth region 402h, a ninth region 402i, a tenth region 402j, an eleventh region 402k, and a twelfth region 402l. Although the illustrated embodiment includes twelve (12) regions 402, the resistance temperature detector 400 may include any number of regions 402 in other embodiments. In some embodiments, each of the regions 402 may have a generally rectangular shape, although other shapes of the regions 402 may be used in other embodiments. In some embodiments, all of the regions 402 may have the same shape and the same size. In other embodiments, some of the regions 402 may have the same shape and the same size, while other regions 402 may have a different shape and/or a different size.

In some embodiments, each region 402 of the resistance temperature detector 400 may be formed by or may include a continuous length of insulated wire 410 having a first end 412 and a second end 414. As shown, the first region 402a may be formed by a first insulated wire 410a, the second region 402b may be formed by a second insulated wire 410b, the third region 402c may be formed by a third insulated wire 410c, the fourth region 402d may be formed by a fourth insulated wire 410d, the fifth region 402e may be formed by a fifth insulated wire 410e, the sixth region 402f may be formed by a sixth insulated wire 410f, the seventh region 402g may be formed by a seventh insulated wire 410g, the eighth region 402h may be formed by an eighth insulated wire 410h, the ninth region 402i may be formed by a ninth insulated wire 410i, the tenth region 402j may be formed by a tenth insulated wire 410j, the eleventh region 402k may be formed by an eleventh insulated wire 410k, and the twelfth region 402l may be formed by a twelfth insulated wire 410l. In other embodiments, each region 402 may be formed by or may include a plurality of insulated wires 410. In some embodiments, for each region 402, the insulated wire 410 thereof may be arranged to form a mesh structure with respective sections of the insulating wire 410 overlapping and contacting one another. In other words, each insulated wire 410 may be arranged to form a mesh structure of the respective region 402. In other embodiments, for each region 402, the insulated wire 410 thereof may be arranged in a manner different from a mesh structure. Each of the insulated wires 410 generally may be formed in a manner similar to the insulated wire 110 described above.

The resistance temperature detector 400 may have a first side 422 (which also may be referred to as a "top side") and a second side 424 (which also may be referred to as a "bottom side") disposed opposite one another. As shown, each of the regions 402 may define a respective portion of the first side 422 and a respective portion of the second side 424. In other words, each of the regions 402 may extend from the first side 422 to the second side 424. As shown, the regions 402 may be arranged in a non-overlapping manner in the direction from the first side 422 to the second side 424. In other words, the regions 402 may be arranged such that the regions 402, and the insulated wires 410 thereof, do not overlap one another in the direction from the first side 422 to the second side 424. As shown, adjacent regions 402 may abut one another along respective edges thereof. In this manner, the regions 402 may be arranged in an array, with respective edges of adjacent pairs of regions 402 abutting one another. In some embodiments, the resistance temperature detector 400 may include a pair of lead wires for each region 402, with the lead wires being coupled to the respective ends 412, 414 of the insulated wire 410 of the region 402. The lead wires may be configured for connecting to a resistance module during use of the resistance temperature detector 400.

In various applications, the resistance temperature detector 400 may be used for determining average temperature over a surface of interest. The resistance temperature detector 400 may be positioned over the surface of interest such that each of the insulated wires 410 directly contacts the surface. In particular, the resistance temperature detector 400 may be positioned over the surface of interest such that respective portions of the insulated wires 410 along the first side 422 or the second side 424 of the resistance temperature detector 400 directly contact the surface. In some embodiments, a majority of the length of each of the insulated wires 410 may directly contact the surface of interest. In some embodiments, the insulated wires 410 may conform to a shape of the surface of interest due to the flexibility of the insulated wires 410. After positioning the resistance temperature detector 400, a resistance of each of the insulated wires 410 may be determined. For example, a resistance module connected to the resistance temperature detector 400 may be used to acquire resistance data for the resistance temperature detector 400 and determine the resistance of each of the insulated wires 410, with the different resistance values corresponding to the respective regions of the surface of interest covered by the respective regions 402 of the resistance temperature detector 400. Then, average surface temperatures of the respective regions of the surface of interest may be determined based at least in part on the respective resistances of the insulated wires 410. For example, as described below, a resistance-temperature relationship for the resistance temperature detector 400 may be used to determine the average surface temperatures based at least in part on the respective resistances of the insulated wires 410. In some embodiments, an average surface temperature of the entire surface of interest also may be determined. For example, the average surface temperature of the entire surface of interest may be determined based at least in part on the average surface temperatures of the respective regions of the surface of interest. In this manner, the resistance temperature detector 400 may be used to obtain overall temperature data for a surface of interest as well as separate temperature data for smaller regions of the surface.

Figure 5:
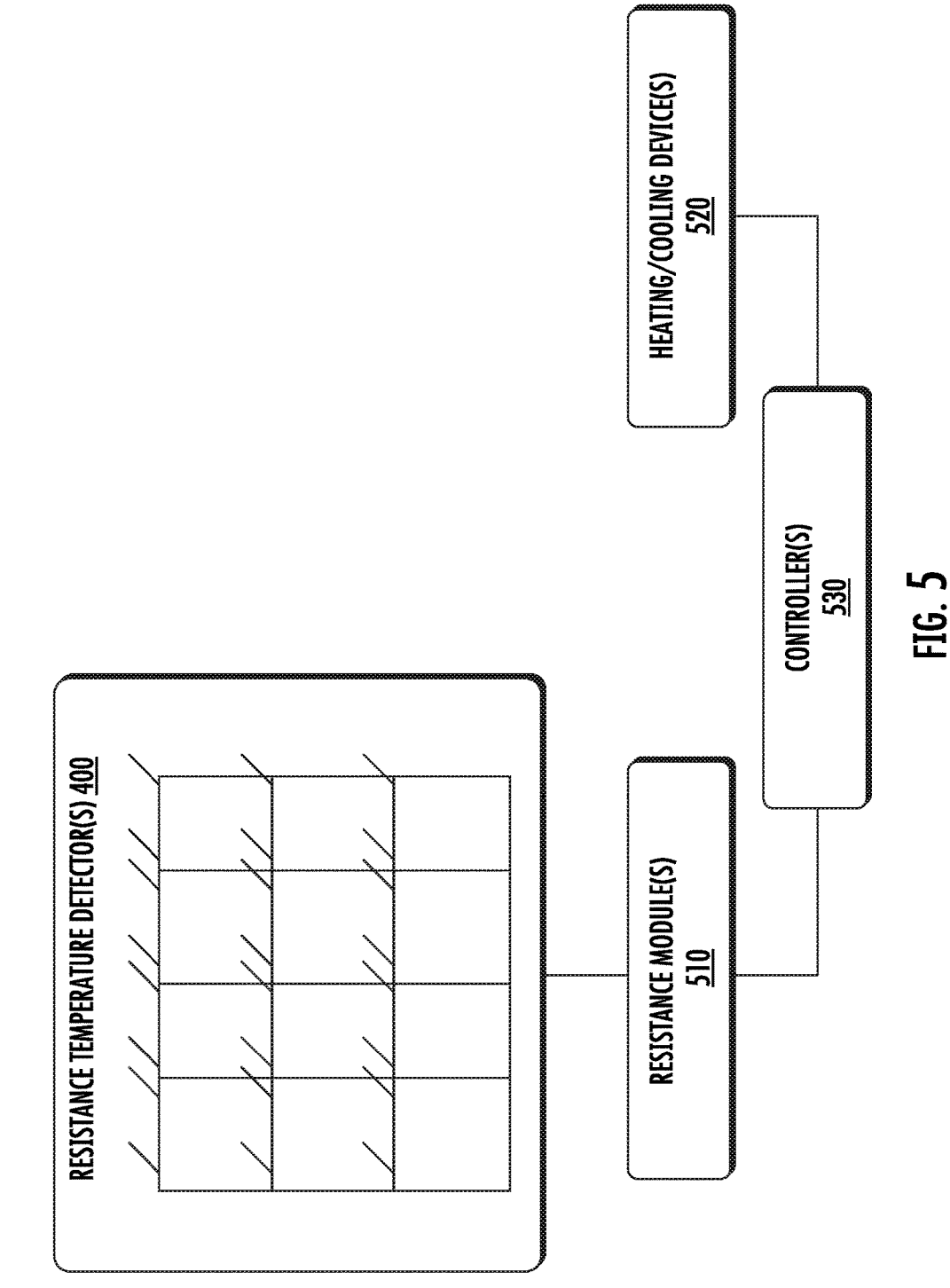
FIG. 5 is a schematic illustration of a system in accordance with one or more embodiments of the disclosure, the system including at least one resistance temperature detector, at least one resistance module, at least one heating or cooling device, and at least one controller.

As shown in FIG. 5, one or more of the resistance temperature detectors 400 may be used as a part of a system 500 in certain applications. In addition to the resistance temperature detector(s) 400, the system 500 may include one or more resistance module(s) 510, one or more heating or cooling device(s) 520, and one or more controller(s) 530. The resistance module(s) 510 may be in operable communication with the resistance temperature detector(s) 400 for acquiring resistance data therefrom. The resistance module(s) 510 may be configured to determine resistance values of the each of the insulated wire(s) 410 of each of the resistance temperature detector(s) 400 during use thereof. The controller(s) 530 may be in operable communication with the resistance module(s) 510 and configured to receive the resistance values therefrom. The heating or cooling device(s) 520 may be configured to heat and/or cool a surface of interest, depending on the particular application. The controller(s) 530 may be in operable communication with the heating or cooling device(s) 520 and configured to adjust a temperature setting of the heating or cooling device(s) 520.

In some embodiments, the system 500 may provide real-time feedback control for regulating a temperature of a surface of interest. As described above, the resistance temperature detector(s) 500 may be positioned over the surface of interest, with the insulated wires 410 directly contacting the surface. The heating or cooling device(s) 520 may be positioned over the surface of interest for heating and/or cooling the surface. In some embodiments, the heating or cooling device(s) 520 may be positioned such that at least a portion of the resistance temperature detector(s) 400 is positioned between the surface of interest and the heating or cooling device(s) 520. In some embodiments, at least a portion of the heating or cooling device(s) 520 may directly contact the surface of interest. For example, respective portions of the heating or cooling device(s) 520 may directly contact the surface of interest through openings of the resistance temperature detector(s) 400. In some embodiments, the heating or cooling device(s) 520 may be positioned such that at least a portion of the heating or cooling device(s) 520 directly contacts the resistance temperature detector(s) 400. During use of the system 500, the controller(s) 530 may receive one or more resistance value(s) from the resistance module(s) 510 and then determine, based at least in part on the resistance value(s), respective average surface temperatures over respective regions of the surface of interest and/or an average surface temperature over the entire surface of interest. For example, the controller(s) 530 may determine the average surface temperature value(s) based on the resistance value(s) and a resistance-temperature relationship for the resistance temperature detector(s) 400. Then, the controller(s) 530 may cause one or more temperature setting(s) of the heating or cooling device(s) 520 to change based at least in part on the average surface temperature value(s). For example, the controller(s) 530 may compare the average surface temperature value(s) to one or more target temperature(s) and then cause the temperature setting(s) of the heating or cooling device(s) 520 to be increased or decreased based on a difference between the average surface temperature value(s)

and the target temperature(s). Such feedback control may be performed continuously or periodically over a period of time to regulate the temperature of the surface of interest.

In some embodiments, the surface of interest may be a contoured surface. In some embodiments, the surface of interest may be an external surface of an object. In some embodiments, the surface of interest may not be an externally visible surface. In other words, the surface of interest may be at least partially covered by an object. In some embodiments, the surface of interest may be an interface between two or more objects. In some embodiments, the surface of interest may be an external surface of a living subject, such as a human subject. For example, the system 500 may be used for monitoring and controlling average skin temperature of a human subject in thermoregulation applications. Various other potential uses and applications of the system 500 will be appreciated by those of ordinary skill in the art.

Example 2D RTDs and Experimental Data

Two example two-dimensional resistance temperature detectors were fabricated by knitting magnet wire (Elektrisola, Boscawen, NH) into mesh structures having custom shapes. Specifically, the mesh structures were formed by conventional hand knitting techniques. See Nawab, Y. et al., 2017, Structural Textile Design: Interlacing and Interlooping, CRC Press, Boca Raton, FL. The shape, size, and stitch density of the example 2D RTDs were chosen for the specific application of measuring mean nonglabrous skin temperature at the interface of a water perfused suit. As discussed above, an accurate measure of mean skin temperature is imperative to research in the field of thermoregulatory control. See Namisnak, L. H. et al., 2019, "Selective Thermal Stimulation Delays the Progression of Vasoconstriction During Body Cooling," *J. Biomech. Eng.*, 141(12), pp. 124504-1-6.

The first 2D RTD was formed using 32-gauge PN155 wire, with a needle size of 4.5 mm, to have 18 columns, 63 rows, an overall width of 9.0 cm, an overall length of 24.8 cm, a stitch density of 5.1 stitches/cm², and a mass of 8.314 g (average mass, with standard deviation of 0.5 g). The second 2D RTD was formed using 36-gauge P155 wire, with a needle size of 5 mm, to have 48 columns, 28 rows, an overall width of 39.8 cm, an overall length of 11.8 cm, a stitch density of 2.9 stitches/cm², and a mass of 6.639 g (average mass, with standard deviation of 0.9 g).

The wire was manufactured to comply with NEMA MW 1000 standards. See National Electrical Manufacturers Association, 2016, "NEMA MW 1000—Magnet Wire." Both P155 and PN155 wire types have an upper temperature rating of 155° C. P155 is copper wire electrically insulated with a thin coating of modified polyester, while PN155 is copper wire electrically insulated with modified polyester and a thin polyamide overcoating. The wire gauges were chosen based on sensitivity over the target temperature range and mechanical durability for this application. The stitch density was calculated by dividing the total number of stitches (columns×rows) by the area of the 2D RTD. Stitch density is affected by the wire tension controlled by the knitter, the needle size, and the wire size. The first 2D RTD and the second 2D RTD were knitted by two different people who inherently held the wire with differing levels of tension. The mass of each of the 2D RTDs was measured five times with a precision scale (Mettler Toledo, Columbus, OH) to determine the average mass and standard deviation noted above. The first 2D RTD and the second 2D RTD are shown in FIGS. 8A and 8B, respectively, along with thermocouples used for the experimental studies described below.

Instrumentation and Data Processing

The 2D RTDs were connected via a 4-wire connection to a 24-bit resistance module, NI-9217 (National Instruments, Austin, TX). Type T thermocouples (made in-house) were attached to a 24-bit thermocouple module, NI-9213 (National Instruments, Austin, TX). Both modules were housed in chassis, cDAQ-9178 (National Instruments, Austin, TX), and connected to a host computer using LabVIEW 2017 (National Instruments, Austin, TX) interface. All data processing was performed in MATLAB® R2019b (MathWorks, Natick, MA).

Calibration

A calibration was conducted to determine the conversion equation from resistance to temperature as well as the accuracy of the 2D RTDs as compared to thermocouples. The 2D RTDs were calibrated in a recirculating water bath, SK-12122-42 (Cole Parmer, Vernon Hills, IL), with 11 copper-constantan thermocouples intertwined in the 2D RTDs. The thermocouples were previously calibrated in an ice point calibration chamber, TRCIII (Omega, Norwalk, CT). The accuracy and precision of the thermocouples were 0.20° C. and respectively. The calibration of 2D RTDs was performed beyond the temperature range for safe tissue exposure to confirm the device performance in a broader context. See Hall, J. E., 2016, "Functional Organization of the Human Body and Control of the 'Internal Environment, '" *Guyton and Hall Textbook of Medical Physiology*, Elsevier, Philadelphia, PA, pp. 3-10.

Figure 6:
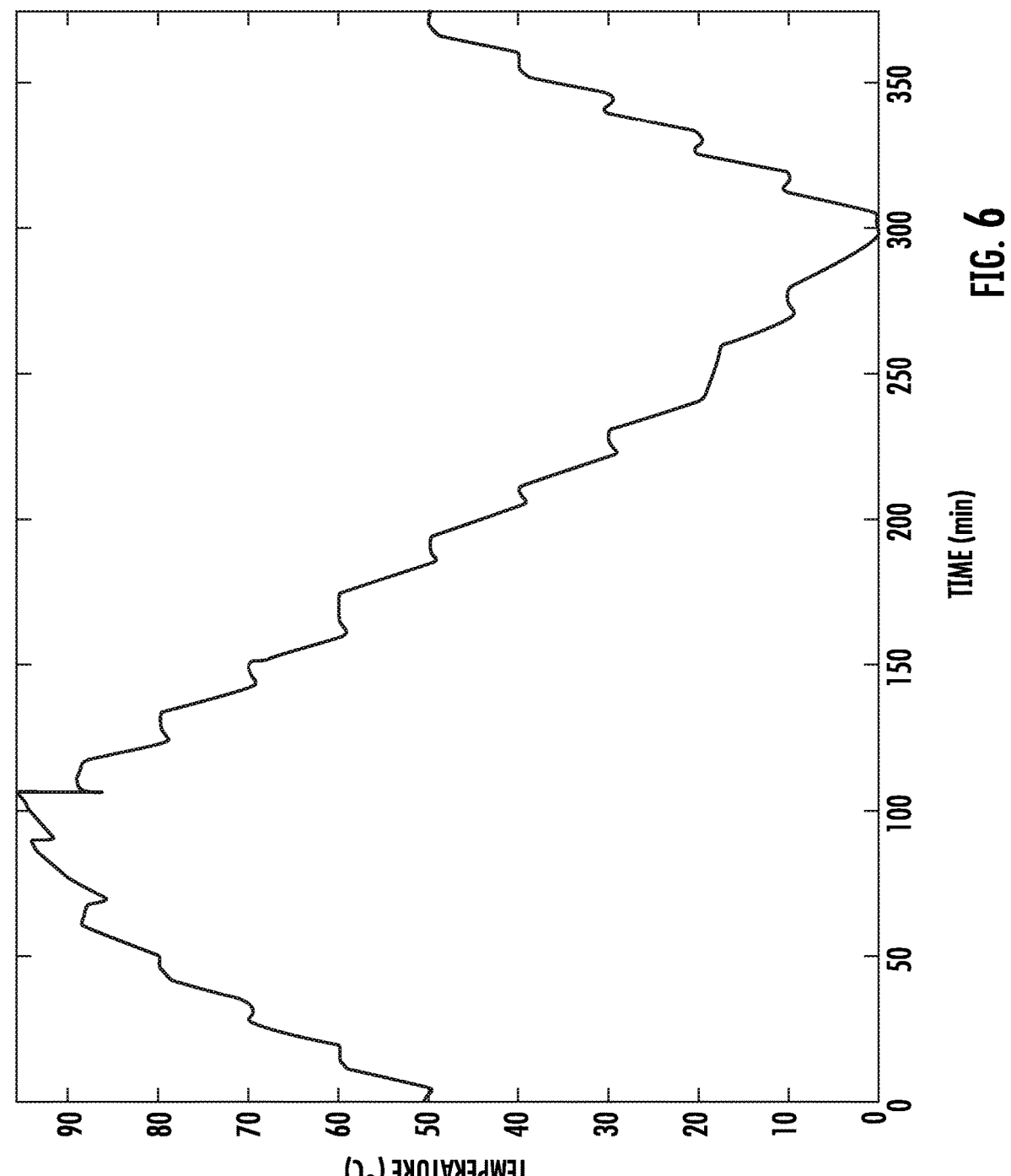
FIG. 6 is a graph of temperature as a function of time, illustrating an example calibration of a two-dimensional resistance temperature detector in accordance with one or more embodiments of the disclosure.

A first calibration was performed on both the first 2D RTD and the second 2D RTD in a 20/80 (by weight) glycerin/water solution (Glycerin Supplier, Houston, TX) in a temperature range spanning 0-100° C. The freezing point to boiling point temperature range for the 20/80 solution was −4.8-101.6° C. See Glycerine Producers' Assosiation, 1963, Physical Properties of Glycerine and Its Solutions, Glycerine Producers' Association, New York. The temperature profile for this experiment is shown in FIG. 6. The calibration began at a temperature of 50° C. The bath temperature was increased to 99.6° C., decreased to 0° C., and then reheated to 50° C. Temperature was stabilized in the circulating bath for 5 minutes at each 10° C. interval so steady state data was collected for calibration and to investigate possible hysteresis. As bath temperature approached boiling and water evaporated from the water bath, room temperature makeup water was introduced into the bath, resulting in periods when the bulk solution was not a uniform temperature which caused outliers in temperature data, which were removed from the analysis.

Figure 7:
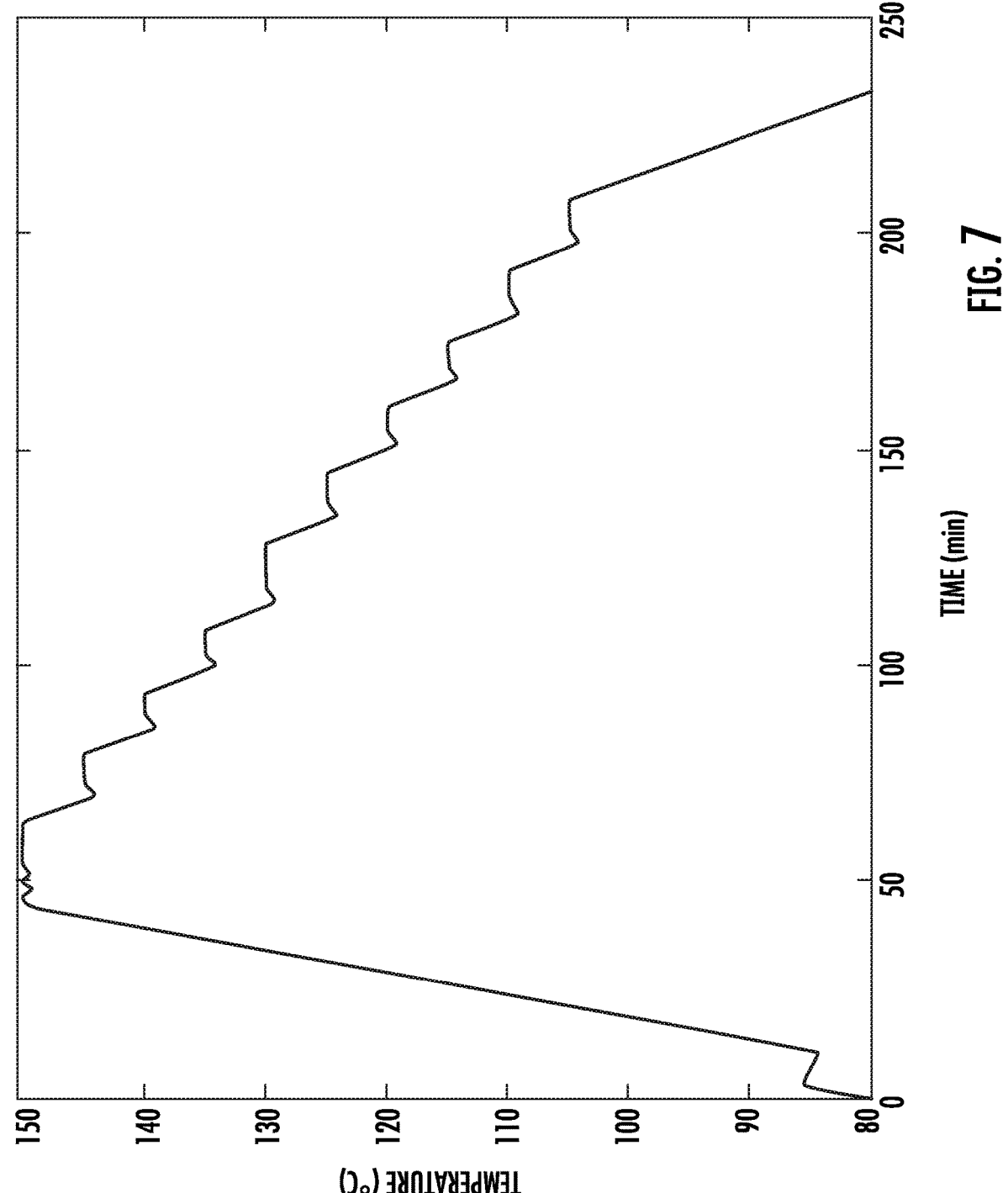
FIG. 7 is a graph of temperature as a function of time, illustrating an example calibration of a two-dimensional resistance temperature detector in accordance with one or more embodiments of the disclosure.

A second calibration was conducted on the second 2D RTD in the heated circulating bath filled with undiluted glycerin with a boiling temperature of 290° C., over a temperature range of 90-150° C. See id. Temperature was increased continuously from 90 to 150° C., then decreased to 90° C. with stabilization periods at 5° C. intervals until 105° C. was established, and then linearly decreased beyond 95° C. The measured temperature profile is shown in FIG. 7.

Calibration curves for temperature as a function of electrical resistance were calculated using the lower temperature data set for the first 2D RTD and both data sets combined for the second 2D RTD. After removal of outlier data, thermocouple temperature and resistance data, which were sampled at a rate of 10 Hz, were extracted at 0.01° C. increments. That data was used to fit temperature to resistance over the calibration range using a linear function.

Resistance and temperature vary linearly in the range of 0-150° C. See United States. National Bureau of Standards and Institute for Applied Technology (U.S.), Office of Engineering Standards, 1966, *Copper Wire Tables*, National Bureau of Standards. The relationship between resistance and temperature is shown in Equation 1 (below), where R is resistance, T is temperature, $R_{ref}$ and $\alpha_{ref}$ are the resistance and temperature coefficient of resistance at the reference temperature, $T_{ref}$. The temperature coefficient of resistance at 20° C. has been reported over the wide range of 0.00369-0.00409° $C.^{-1}$. See Dellinger, J. H., 1911, *The Temperature Coefficient of Resistance of Copper*, U.S. Government Printing Office. For the 2D RTDs, $\alpha_{20}$ was calculated by rearranging Equation 1 into Equation 2 (below) for a reference temperature of 20° C.

$$R(T)=R_{ref}(1+\alpha_{ref}(T-T_{ref})) \tag{1}$$

$$\alpha_{ref}=(R-R_{20})/(R_{20}(T-20)) \tag{2}$$

Figure 9B:
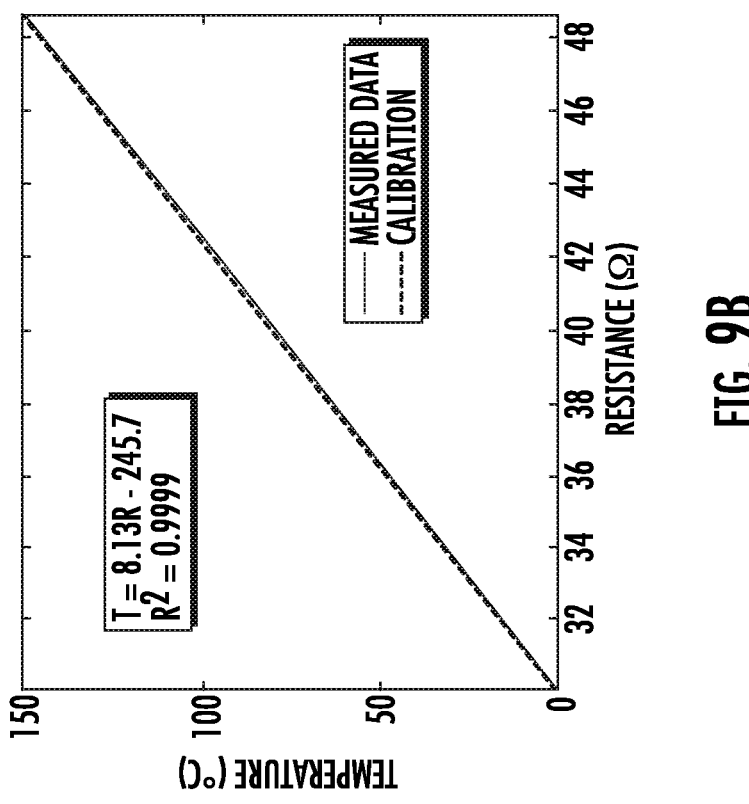
FIG. 9B is a graph of temperature as a function of resistance, illustrating an example calibration curve for the second two-dimensional resistance temperature detector.
Figure 9A:
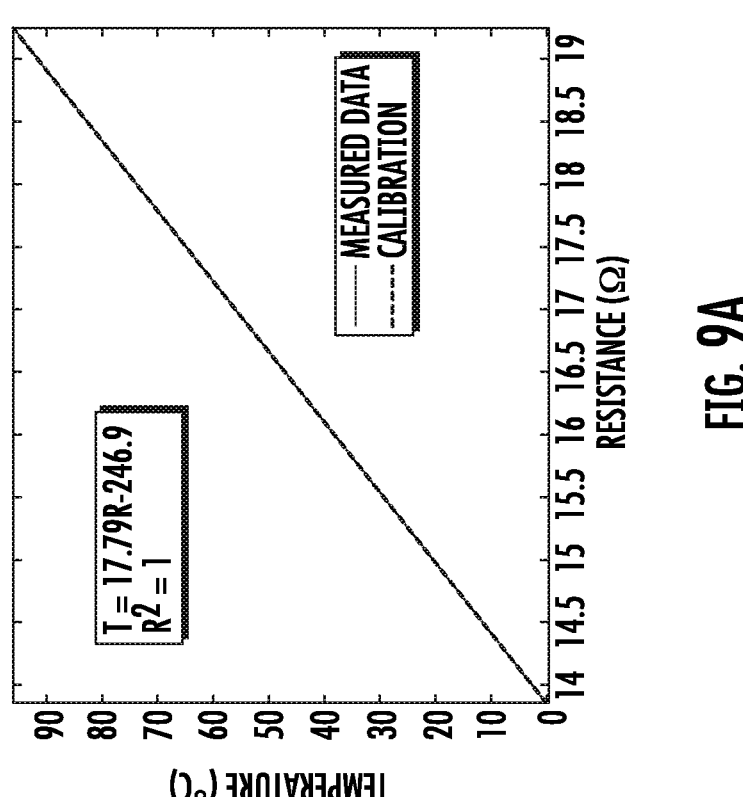
FIG. 9A is a graph of temperature as a function of resistance, illustrating an example calibration curve for the first two-dimensional resistance temperature detector.

FIGS. 9A and 9B show the calibration curves of resistance as a function of temperature for the first 2D RTD and the second 2D RTD, respectively. The size of the resistance and temperature vectors used for calibration were 9589 and 14980 data points for the first 2D RTD and the second 2D RTD, respectively. However, the vectors were downsampled to every 400th data point for the illustrated plots. The coefficient of determination was 1 and 0.9999 for the first 2D RTD (FIG. 9A) and the second 2D RTD (FIG. 9B), respectively, indicating that the calibrated 2D RTDs have an accuracy of at least 99.99% of that of thermocouples. The thermocouples used in this study had a calibrated accuracy of 0.2° C. at 0° C. Based on Equation 2, the temperature coefficient of resistance for the first 2D RTD and the second 2D RTD were calculated to be 0.00375° $C.^{-1}$ and 0.00376° $C.^{-1}$, respectively.

Hysteresis

Figure 10:
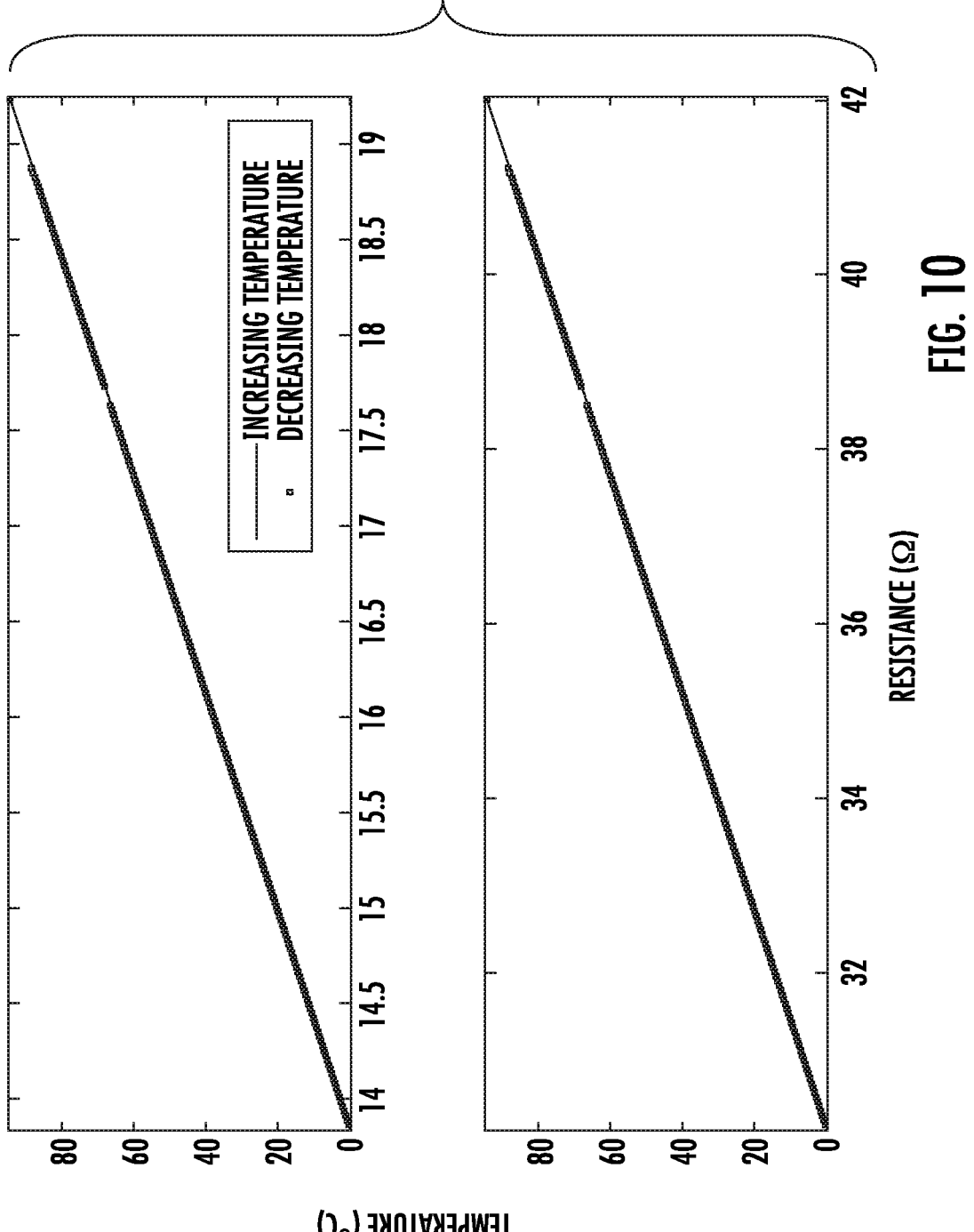
FIG. 10 is a graph of temperature as a function of resistance, illustrating example temperature-resistance relationships for the first two-dimensional resistance temperature detector (upper) and the second two-dimensional resistance temperature detector (lower).

The experimental data collected for calibration was used to investigate the existence of hysteresis in temperature measurements between heating and cooling. Temperature and resistance data were extracted for the portion of the experiment in which temperature was increasing and separately for the period while temperature was decreasing. Resistance is shown in FIG. 10 to be a function of temperature for both sets of data (heating and cooling) for both the first 2D RTD (upper plot) and the second 2D RTD (lower plot) to provide for a visual representation of hysteresis. The plots in FIG. 10 show the resistance-temperature relationship as temperature was alternatively increased and decreased for both of the 2D RTDs. The decreasing temperature plots overlay the increasing temperature plots in FIG. 10, showing no discernable hysteresis.

Comparison of Two-Dimensional to One-Dimensional Measurement

The calibration curve was used to compare the 2D RTDs and thermocouple temperatures under a water perfused garment (MED-ENG, Ottawa, Canada) used in thermoregulation testing. The purpose of this test was to highlight the large spatial differences in temperature detected by point sensors applied to a nonuniform surface. The experiment was run by mounting the 2D RTDs and multiple thermocouples onto a substrate material with uniform thermal properties. Three thermocouples were attached at discrete points to the first 2D RTD, as shown in FIG. 8A, and six thermocouples were interspersed over the area covered by the second 2D RTD, as shown in FIG. 8B. A water-perfused suit was placed over the 2D RTDs to create a nonuniform temperature field as encountered during thermally based medical procedures. A recirculating water bath was attached to the garment. The protocol for the first 2D RTD consisted of a five-minute baseline period with no water running through the suit followed by 65 minutes of cooling with ice water. The second 2D RTD was exposed to approximately 40° C. water flowing through the tubes for 15 minutes followed by 55 minutes of cooling by ice bath after which the garment was slightly repositioned to highlight the sensitivity of point sensors to lateral temperature variations compared to the surface area sensor that intrinsically averages temperature across its entire length. The temperature measurements were verified by infrared thermography. A thermal image was taken of the surface of the suit adjacent to the second 2D RTD at the end of the second 2D RTD experiment with infrared camera, T620 (FLIR, Wilsonville, OR).

Figures 11A, 11B:
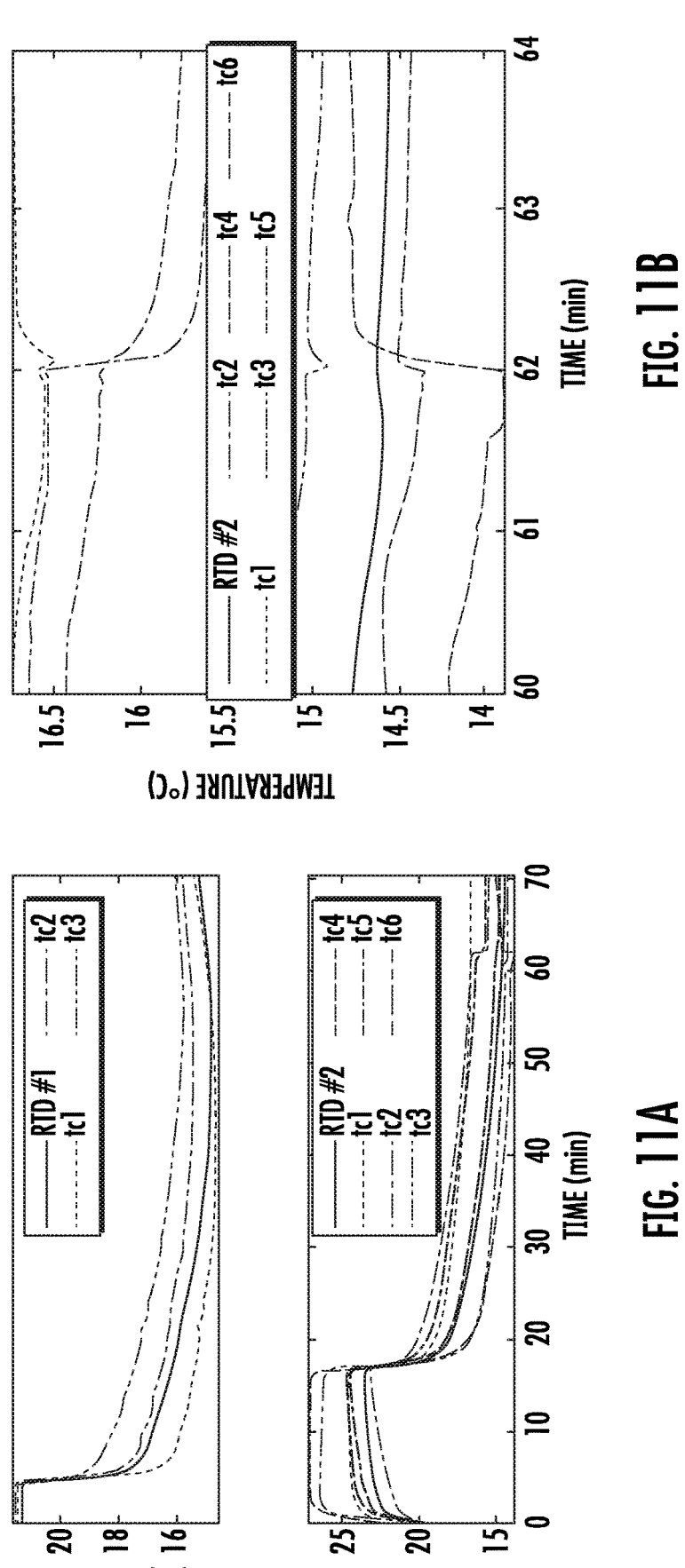
FIG. 11A is a graph of temperature as a function of time, illustrating example temperature data obtained using a plurality of thermocouples, the first two-dimensional resistance temperature detector, and the second two-dimensional resistance temperature detector.
FIG. 11B shows a detailed portion of the graph of FIG. 11A.
Figure 12:
FIG. 12 is an infrared image of a portion of a water-perfused suit showing example temperature data obtained using infrared thermography.

FIG. 11A shows the single point thermocouple measurements obtained while intertwined in the 2D RTDs, as shown in FIGS. 8A and 8B, and the average surface area measurement by the 2D RTDs while ice water was pumped through the water perfused garment. The upper plot, for the first 2D RTD, shows a maximum temperature difference of 2.5° C. between the highest and lowest temperatures sensed by the thermocouples at 8.8 minutes. The lower plot, for the second 2D RTD, shows a 5.4° C. maximum difference during warming at 2 minutes. FIG. 11B shows an exploded view of the lower plot of FIG. 11A for the second 2D RTD between 60 and 64 minutes. While there was minimal change in temperature of the water flowing through the garment, there was a marked change in each thermocouple reading after moving the suit. The temperature reading by the second 2D RTD remained within the range of thermocouple temperatures throughout the experiment and was not sensitive to movement of the suit. FIG. 12 shows an IR image of the suit at the end of the experiment on the second 2D RTD. The region covering the second 2D RTD is outlined. The average temperature using the IR camera for the area covering the second 2D RTD was 14.1° C. on the IR image and 14.5° C. by the second 2D RTD, as shown in the lower plot of FIG. 11A, well within the ±2° C. accuracy of the thermal camera. FIG. 12 shows the two-dimensional temperature variation from the outlined area in the IR image. The maximum temperature difference as detected by IR thermography was 7.5° C.

Comparison to Wearable Sensors

Figure 13B:
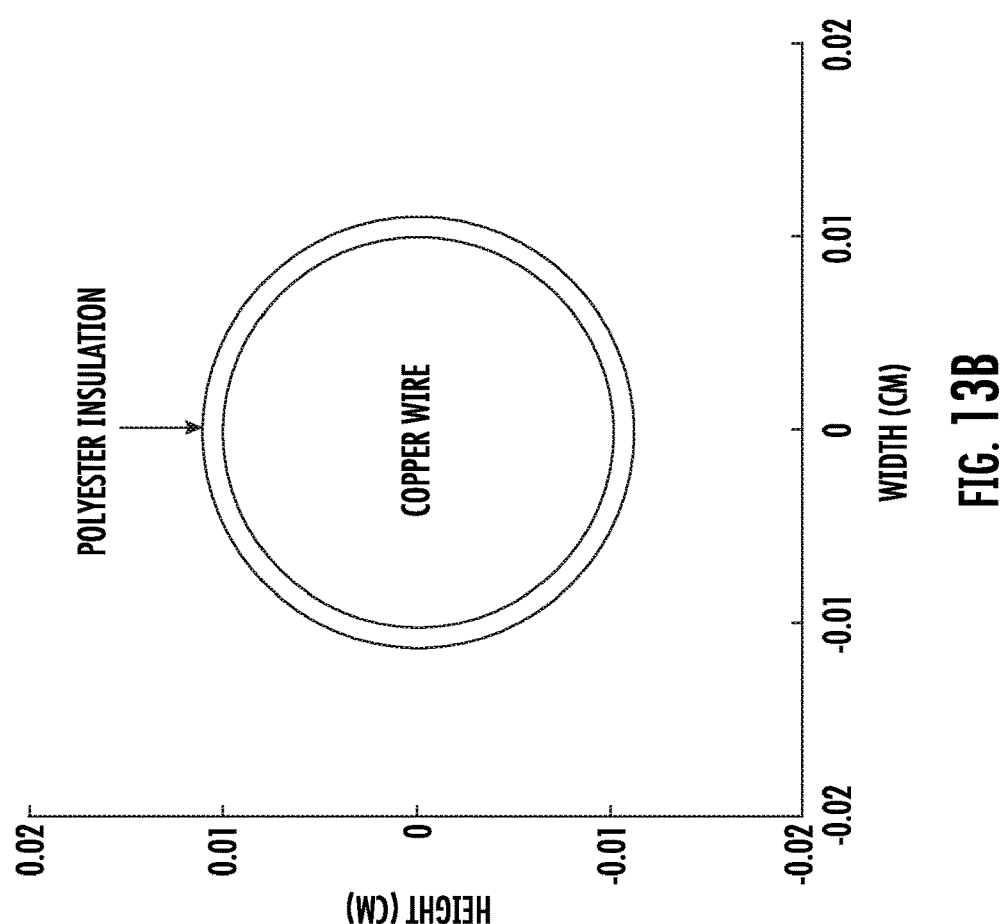
FIG. 13B is a schematic illustration of an example model of a sensor.
Figure 13A:
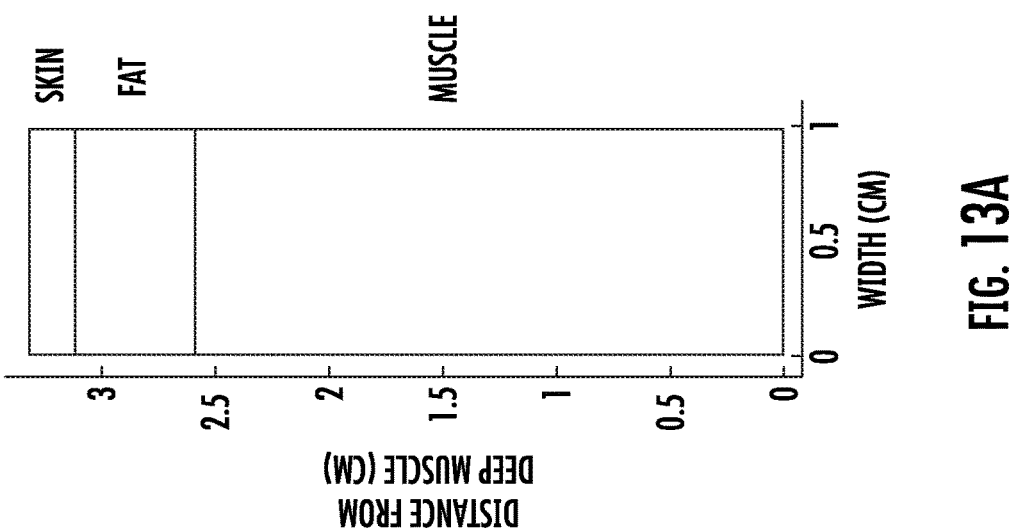
FIG. 13A is a schematic illustration of an example model of biological tissue adapted from Fiala's leg cylinder.

As discussed above, many wearable sensors that measure skin temperature for medical applications may consist of a thermally sensitive wire incorporated into a substrate material. The substrate material introduces a layer of thermal insulation which impedes the heat transfer between the environment and the skin, which is dependent on the thickness of the insulation. Even with a decreased heat transfer, the sensor could accurately detect the skin temperature if there is direct contact. However, it is also possible that the sensor is embedded in the substrate material without direct access to the skin, causing a less accurate measure of skin temperature. Simulations were conducted comparing the 2D RTD to temperature sensors incorporated into a substrate layer. The simulations detected the effective heat loss caused by two different thicknesses of thermal insulation while the sensor is in direct contact with the skin. Additional simulations were performed to determine the discrepancy between sensor and skin temperature when the sensor is embedded in the substrate material at two different distances from the skin. All simulations were conducted in COMSOL Multiphysics® v. 5.5. See COMSOL Multiphysics® v. 5.5. www.comsol.com. COMSOL AB, Stockholm, Sweden. Each model had the same biological tissue geometry, as shown in FIG. 13A. The model incorporated a composite tissue consisting of layered muscle, fat, and skin as adapted from Fiala's leg cylinder. See Fiala, D. et al., 1999, "A Computer Model of Human Thermoregulation for a Wide Range of Environmental Conditions: The Passive System," *J. Appl. Physiol.*, 87(5), pp. 1957-1972. Deep muscle tissue was assumed to be maintained at central temperature by deep layer blood perfusion. Tissue properties that were not included in the COMSOL Multiphysics® library, but necessary for the simulation, include heat capacity of blood, blood density as well as blood perfusion rate and metabolic heat generation rate for each tissue type. See Namisnak, L. H. et al. These properties were extracted from the IT'IS Foundation database. See Hasgall, P. et al., 2018, IT'IS Database for Thermal and Electromagnetic Parameters of Biological Tissues. The sensor models represented varying insulation thicknesses and placement of the senor within the polyester insulation, but the sensor was consistently a 32 AWG cross section of copper magnet wire with polyester electrical insulation, as shown in FIG. 13B. The width of the tissue model was 1 cm, which is more than an order of magnitude larger than the diameter of the electrically insulated wire, which was 0.224 mm. This geometry ensured that far field influences do not affect thermocouple measurements in the model solution.

A first set of simulations was conducted to assess the effect of insulation thickness on the heat flow from the environment to the surface of the skin. Three sensor configurations were created, as shown in FIG. 14A. A control model (lower) contained no thermal insulation and was representative of the 2D RTD. Two intervention models included polyester insulation layers of 1 mm (middle) and 2 mm (upper), respectively. See Husain, M. D. et al.; Oglakcioglu, N. et al., 2007, "Thermal Comfort Properties of Some Knitted Structures," *Fibres Text. East. Eur.*, (Nr 5-6 (64)), pp. 94-96. The three simulations were conducted by adding a sensor, as shown in FIG. 14A, to the surface of the skin, as shown in FIG. 13A. The inner boundary condition at the deep muscle was set to a constant temperature of 37° C., while the surface boundary condition (either surface of the skin and the upper half of the magnet wire insulation or surface of polyester insulation) was set to 43° C. as may be imposed by the environment. A zero-flux boundary condition was selected for the outer left and right boundaries. After the steady state temperature profile for each model was determined, the temperature difference between the thermally insulated models and the uninsulated model was calculated to describe the effects of the thickness of the polyester insulation as the substrate material for which the sensor was embedded.

Figure 14B:
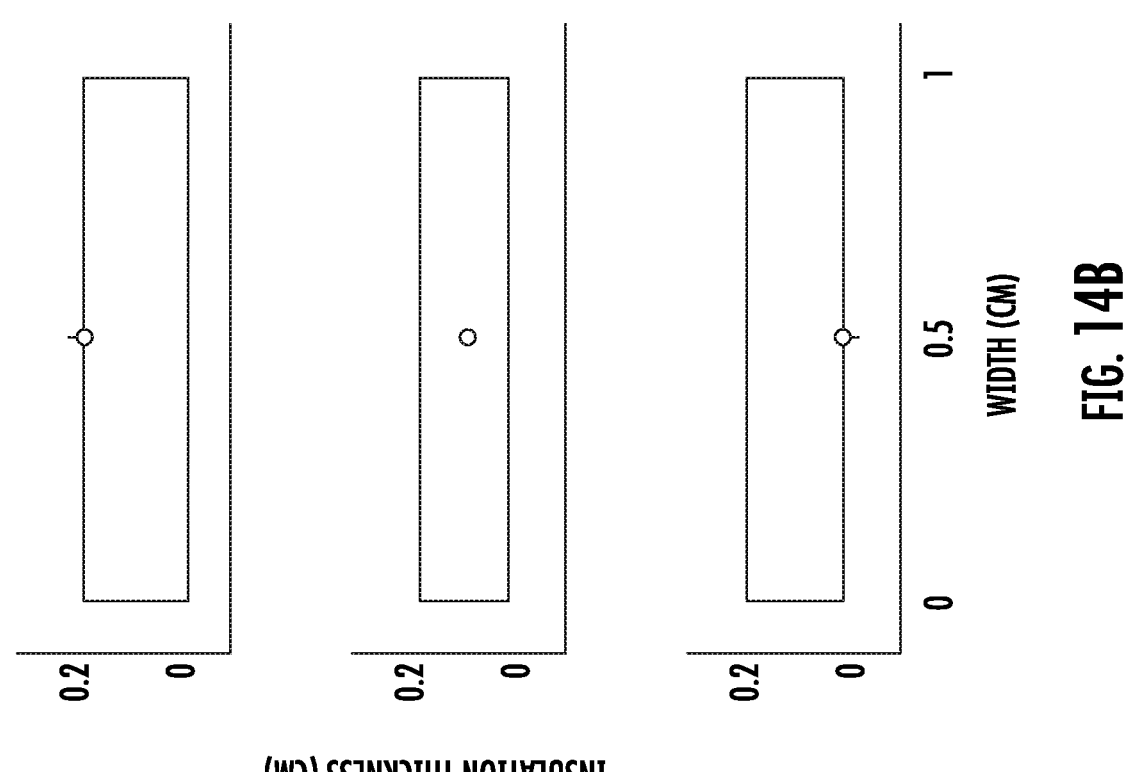
FIG. 14B is a schematic illustration of example models of a sensor located at a bottom surface of an insulation layer (lower), a sensor embedded within an insulation layer (middle), and a sensor located at a top superficial surface of an insulation layer (upper).
Figure 14A:
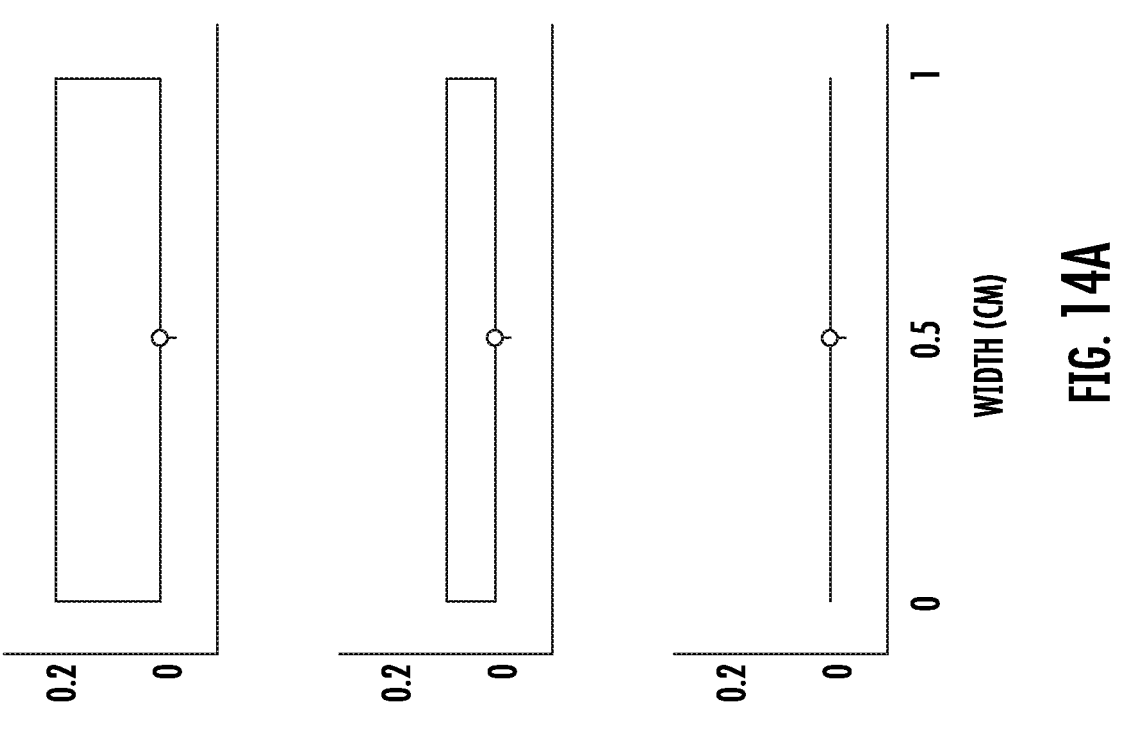
FIG. 14A is a schematic illustration of example models of a sensor with no insulation (lower), a sensor with 1 mm of insulation (middle), and a sensor with 2 mm of insulation (upper).

A second set of simulations was conducted to determine the discrepancy between superficial skin temperature and the temperature of the copper sensor when the sensor is attached to the substrate material surface or embedded within the material, as shown in FIG. 14B. Each model included a 2 mm layer of polyester insulation to represent the substrate material. Prior to the simulation, a sensor was added to the surface of the skin, as shown in FIG. 13A. For control conditions, the wire sensor was positioned directly at the interface of the skin and the thermal insulation layer, as shown in the lower portion of FIG. 14B. Two intervention models placed the wire sensor midway through the thermal insulation layer, as shown in the middle portion of FIG. 14B, and at the superficial surface of the insulation layer, as shown in the upper portion of FIG. 14B. A 43° C. constant temperature boundary condition was set at the outer surface for each model. The temperature at the base of the muscle layer was set to 37° C. After the steady state temperature profile was determined, the difference between the temperatures of the copper wire and of the surface of the skin was calculated to indicate the accuracy of the measurement configuration.

Figure 15:
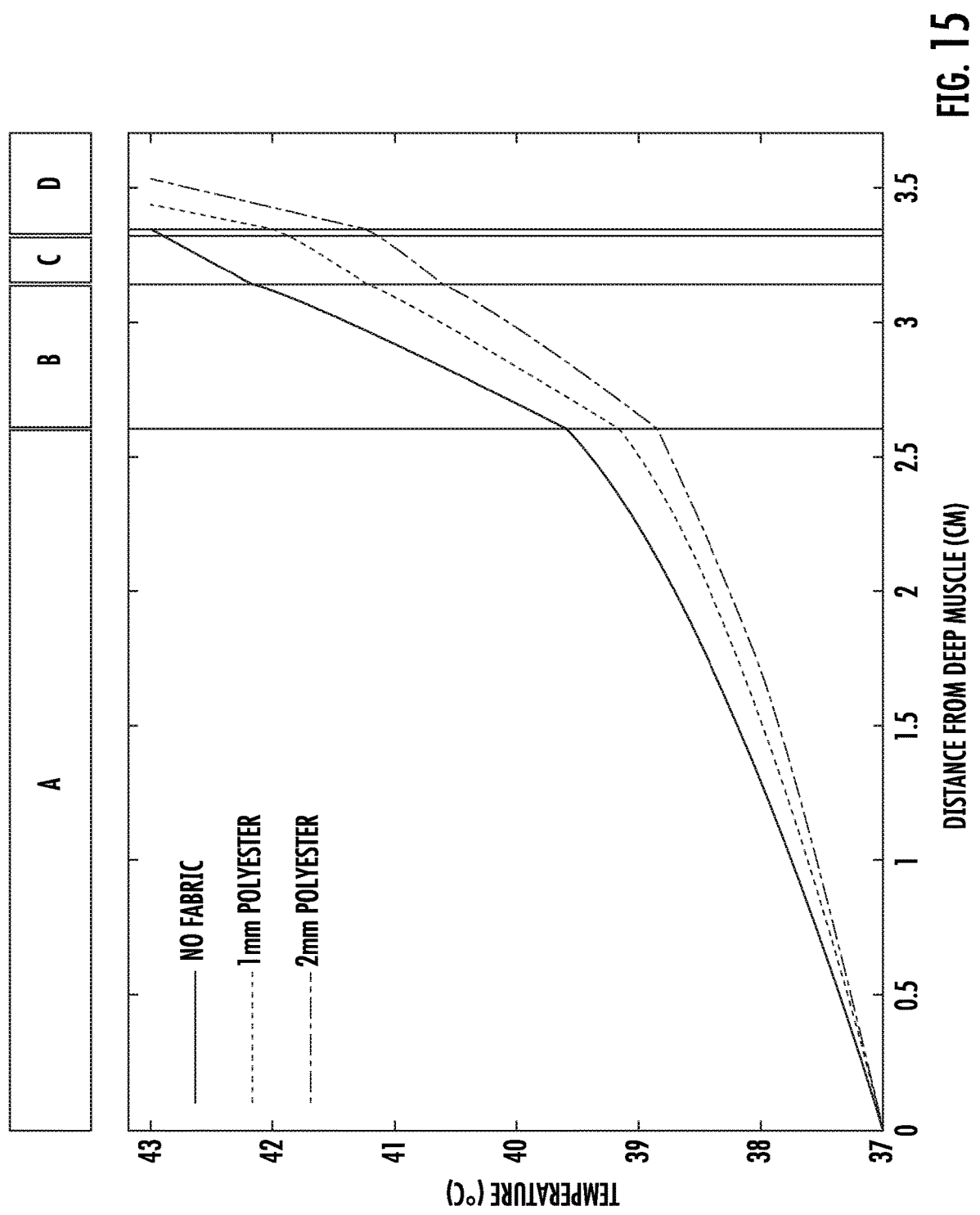
FIG. 15 is a graph of centerline temperature as a function of distance from deep muscle, illustrating example temperature data corresponding to the sensor models of FIG. 14A.

The centerline (x=0.5 cm) temperature for each COMSOL Multiphysics® model for which the copper wire was located between the skin and the polyester thermal insulation is plotted in FIG. 15. See Namisnak et al. In FIG. 15, A is the muscle layer, B is the fat layer, C is the skin layer, D is the thermal insulation layer, and the distance between C and D is the diameter of the magnet wire (0.224 mm). The skin surface temperatures for the control, 1 mm of insulation, and 2 mm of insulation models were 43.0° C., 42.0° C., and 41.2° C., respectively. Including 1 mm and 2 mm of insulation between a constant temperature heat source and the surface of the skin resulted in a skin temperature of 1.0° C. and 1.8° C. less than a skin temperature unaffected by thermal insulation, respectively. The temperature range from deep muscle to surface was 6° C. Therefore, the energy transferred to the tissue was 83.3% and 70.0% of the total energy input to the system when 1 mm and 2 mm of insulation were included in the system, respectively. Transversely, 16.7% and 30% of the input energy was lost to 1 mm and 2 mm of insulation, respectively.

Figure 16:
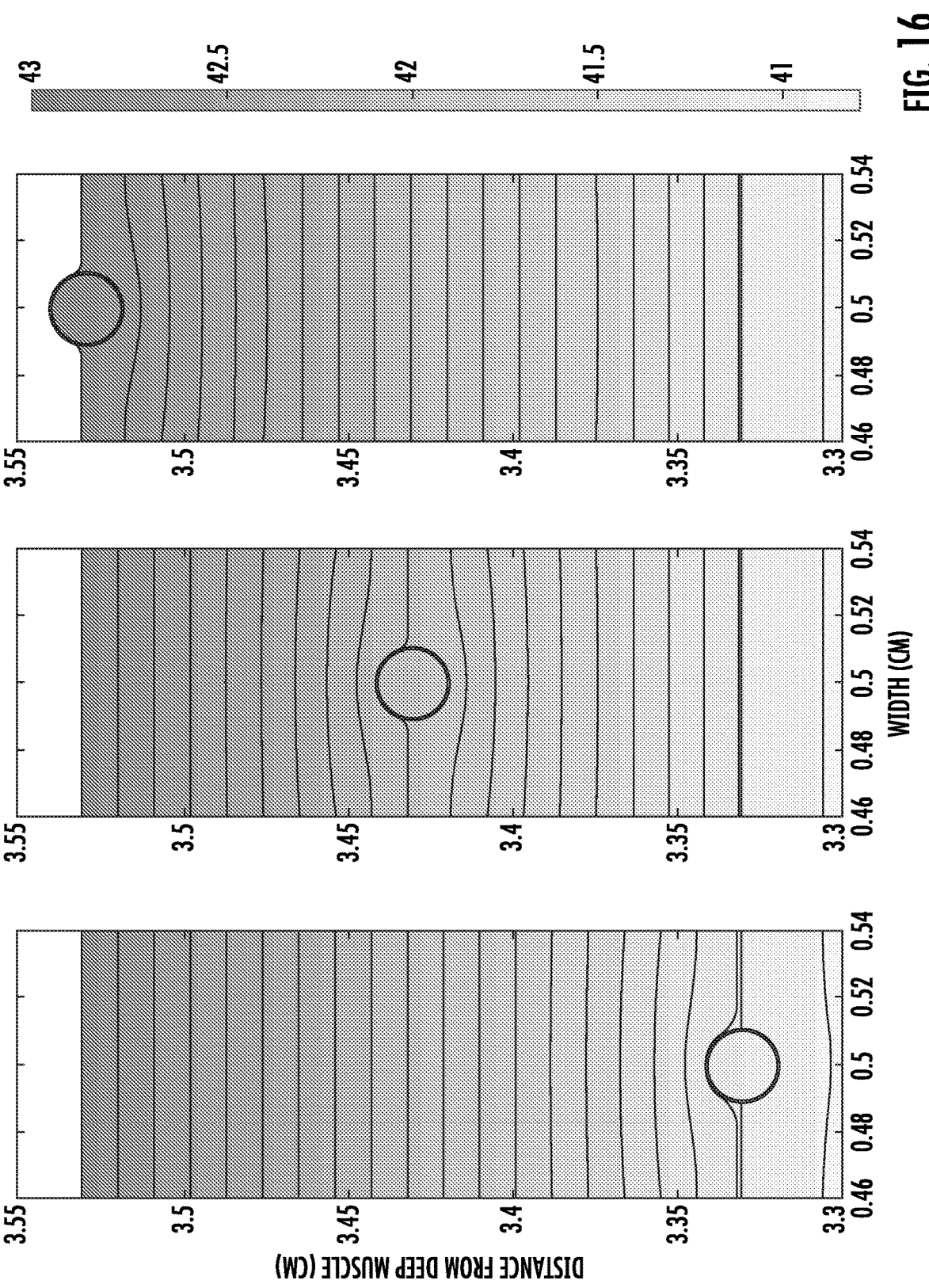
FIG. 16 illustrates example temperature data corresponding to the sensor models of FIG. 14B, with the sensor located at the bottom surface of the insulation layer (left), the sensor embedded within the insulation layer (middle), and the sensor located at the top superficial surface of the insulation layer (right).
Figure 17:
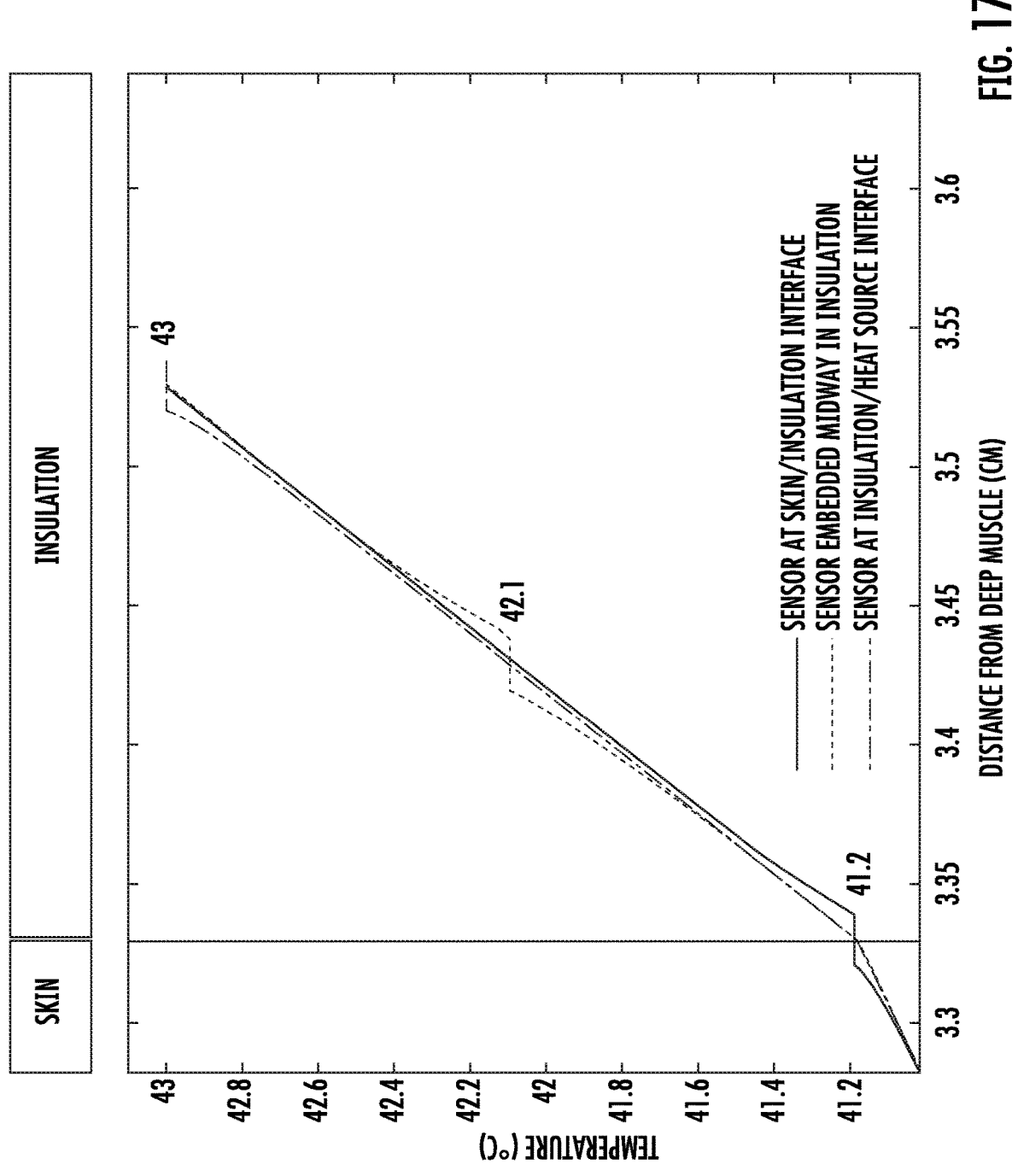
FIG. 17 is a graph of centerline temperature as a function of distance from deep muscle, illustrating example temperature data corresponding to the sensor models of FIG. 14B.

The model results shown in FIG. 16 include 0.04 cm superficial skin, a 2 mm layer of polyester, and a wire temperature sensor located alternately, at the skin/insulation interface, 1 mm into the insulation layer, or at the surface of the insulation adjacent to a constant temperature heat source. FIG. 17 shows the centerline (x=0.5 cm) temperature of each of the 3 models. The temperature in the copper wire was 41.2° C., 42.1° C., and 43° C. for the three cases, as shown in FIG. 16. The skin temperature for each of the 3 models was 41.2° C. When embedded midway through a 2 mm polyester substrate material, the sensor error was 0.9° C. When the wire sensor was located at the surface opposite the skin, the sensor error was 1.8° C.

Repeatability

Figure 18:
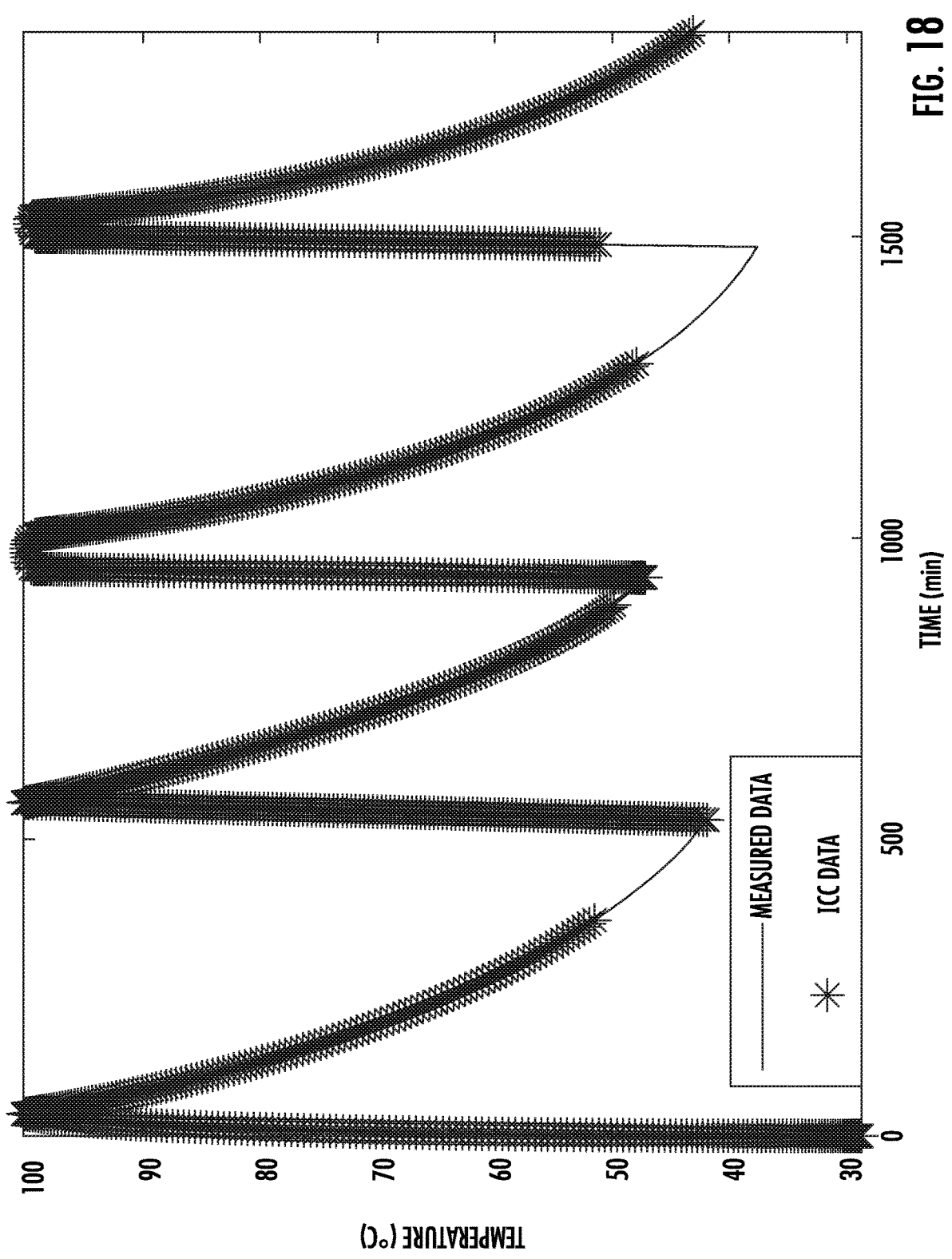
FIG. 18 is a graph of temperature as a function of time, illustrating example temperature data obtained during a repeatability study using the second two-dimensional resistance temperature detector.
Figure 19:
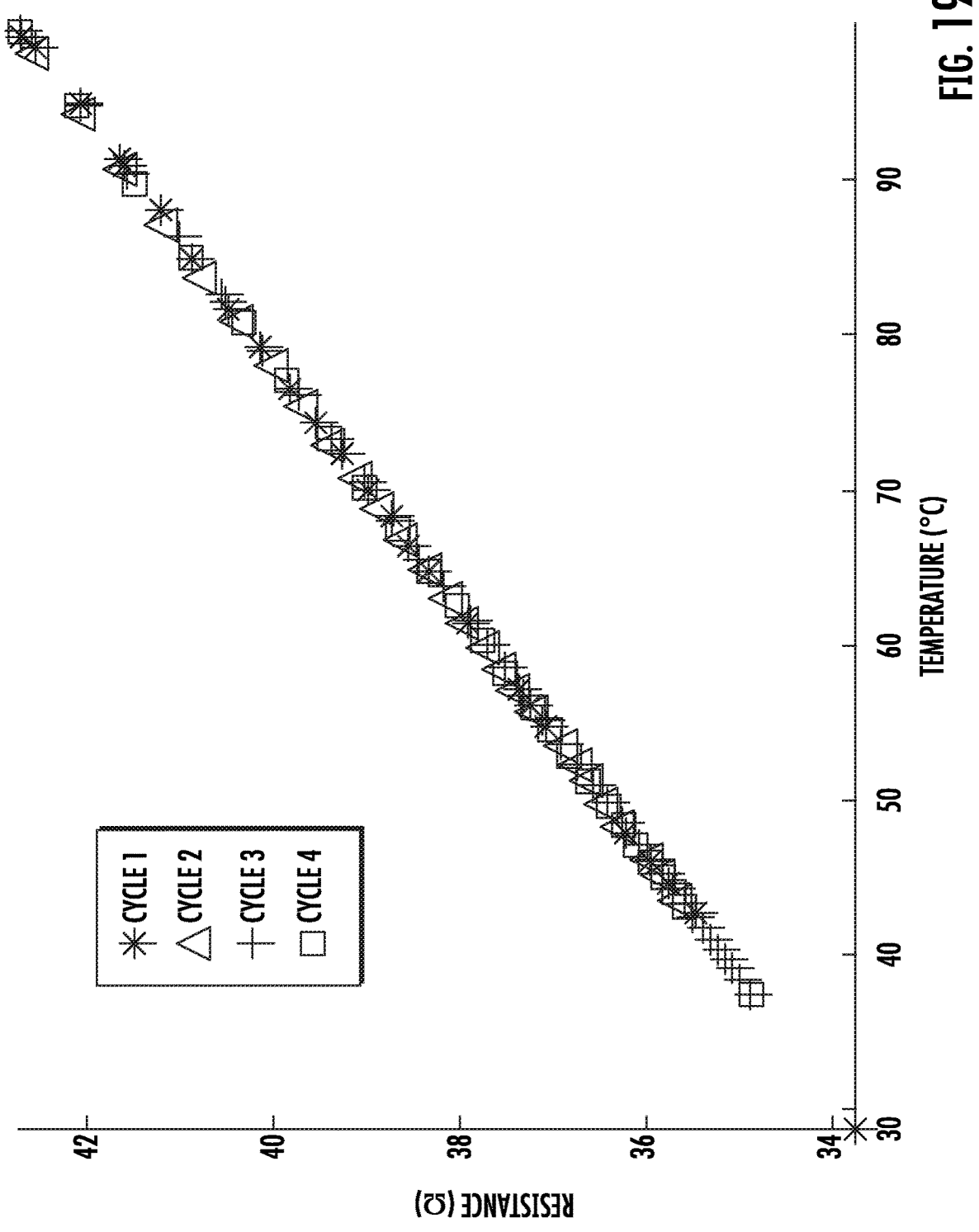
FIG. 19 is a graph of resistance as a function of temperature, illustrating example resistance data obtained during the repeatability study using the second two-dimensional resistance temperature detector.

An experiment was conducted with the second 2D RTD to test the repeatability of the sensor while cycling the temperature of a water bath (Instant Pot, Ottawa, ON, Canada) between approximately 45° C. and 100° C. Data was collected at 1 Hz. The average (±SD) duration of each cycle was 460 (±92) minutes. For data processing, the cycle duration was decreased to 357 minutes to create equally sized vectors for intraclass correlation (ICC) analysis. The vectors were defined by the shortest duration of heating and cooling and subtracting and adding that time from the time the peak occurred, respectively. The vectors were defined by the shortest duration of heating and cooling and subtracting and adding that time from the time the peak occurred, respectively. FIG. 18 shows the data collected during the experiment and the data used for the ICC calculation. The ICC coefficient was calculated with output data from a one-way analysis of variance. See Koo, T. K. et al., 2016, "A Guideline of Selecting and Reporting Intraclass Correlation Coefficients for Reliability Research," *J. Chiropr. Med.*, 15(2), pp. 155-163.

FIG. 20 shows resistance plotted as a function of temperature for each of four cycles in the repeatability study. The data shown for each cycle was downsampled to every 800th data point. There was no discernable difference in the slope or intercept of the four plots. The repeatability study showed an ICC coefficient of 0.99.

Surface Area Conformation

A 2D RTD was wrapped around an adult human arm to evaluate the ability of the 2D RTD to conform to complex 3D surface morphologies. The 2D RTD was secured at each end with medical tape (Hy-Tape International, Patterson, NY).

The photographs in FIGS. 20A and 20B show the 2D RTD wrapped around a human arm which has a relatively small radius of curvature. FIG. 20A shows the arm in an extended position, while FIG. 20B shows the arm in a flexed position. Monitoring the average skin temperature over such a morphological structure can be challenging for nearly all sensor techniques, especially when a subject must flex a limb during a protocol. The 2D RTD was observed as being able to conform to this complex geometry with no discernable air gaps and to move with the surface area over which the 2D RTD was applied while maintaining good thermal contact with the skin.

Discussion

For thermoregulation research and medical applications that involve manipulating skin temperature, a sensor that accurately measures mean skin temperature and does not impede heat transfer is necessary. The 2D RTDs described herein may provide a superior surface area temperature sensor compared to existing technologies because the 2D RTDs exhibit excellent agreement with calibration thermocouples, integrate the temperature over a surface, do not inhibit heat transfer between the skin and the environment, show no discernable hysteresis, are repeatable, and conform easily to the complex morphology of the skin surface. Additionally, the materials required for manufacture of the 2D RTDs are readily available and inexpensive, and the manufacturing process is common and uncomplicated.

As discussed above, calibration of the 2D RTDs yielded an excellent agreement with thermocouples (99.99%) as well as a temperature coefficient of resistance of 0.00375° C.$^{-1}$ and 0.00376° C.$^{-1}$ for the first 2D RTD and the second 2D RTD, respectively. Both of these values are well within the range of reported temperature coefficients of resistance for copper. See Dellinger, J. H.

Thermocouples provide accurate temperature detection when the temperature field is uniform. Multiple thermocouples could detect surface temperature if properly positioned and weighed. However, the temperature variation observed above show that it would be incredibly difficult to properly position and weigh single point sensors to measure the average temperature of a medical device used to manipulate skin temperature, such as a water perfused garment.

Wearable skin temperature sensors consisting of a thermally sensitive metal embedded in a substrate material may be used to detect average two-dimensional skin temperature. While the application for which the described 2D RTDs were used does not require mobility, with an appropriate data logging device, they could be configured as a wearable in certain embodiments. A 2D RTD is represented in the lower plot of FIG. 14A, while existing wearable solutions are represented by a simplified COMSOL Multiphysics® model in the middle and upper plots of FIG. 14A and all plots in FIG. 14B. FIG. 15 shows that wearable temperature sensors that are embedded in a substrate material impede the heat transfer between the source and the skin. In addition, FIGS. 16 and 17 show that, depending on the location of the temperature sensing wire in the substrate material, the accuracy of the sensor could be jeopardized.

The substrate material in which many sensors are embedded is integral to its strength and structure. The strength and structure of the 2D RTDs is derived from the knit pattern. A shortcoming of the 2D RTDs is that strength must be counterbalanced with flexibility and sensitivity. These properties can be customized by selecting an appropriate wire gauge and knit density for each specific application.

The 2D RTDs described were manufactured by two novice knitters. To eliminate human error and reduce variability, an industrial knitting machine could be used. This would provide efficiency and consistency in knit density. Additionally, other manufacturing processes could be implemented to create a 2D RTD, such as weaving or crocheting.

There are many applications for which average skin temperature detection is necessary, such as thermoregulation studies and clinical skin temperature manipulation. However, in a clinical setting, measures must be taken to ensure the safety of the patient. The possibility of sensor breakage and electrical interference must be considered. Therefore, the 2D RTDs should not be used near a surgical site, nor in conjunction with sensitive electrical equipment. Additionally, the 2D RTDs should not be used in extreme temperature environments where the insulation could become damaged, such as during electrocauterization. Also, the 2D RTDs may not detect a single point maximum or minimum and should not be used if a treatment modality includes a point source, such as a laser, and is approaching a limit for thermal injury.

The 2D RTDs allow for temperature measurement of nonuniform surfaces, which falls within the accuracy of the thermal camera. The 2D RTDs can be crafted into custom shapes to meet the need of the end user. The applications addressed above relate to skin temperature measurement. However, the linearity of the temperature-resistance relationship was 99.99% from approximately 0° C.-150° C., far exceeding the physiological temperature range. This temperature range allows for the 2D RTDs to be used in many applications in addition to skin temperature monitoring.

Although specific embodiments of the disclosure have been described, one of ordinary skill in the art will recognize that numerous other modifications and alternative embodiments are within the scope of the disclosure. For example, while various illustrative implementations and structures have been described in accordance with embodiments of the disclosure, one of ordinary skill in the art will appreciate that numerous other modifications to the illustrative implementations and structures described herein are also within the scope of this disclosure.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments.

What is claimed is:

1. A two-dimensional resistance temperature detector for determining average temperature over a surface, the two-dimensional resistance temperature detector comprising:

a continuous length of insulated wire having a first end and a second end;

wherein the insulated wire is arranged to form a mesh structure with respective sections of the insulated wire overlapping and contacting one another, wherein the two-dimensional resistance temperature detector is devoid of any fabric material.

2. The two-dimensional resistance temperature detector of claim 1, wherein the insulated wire comprises a metal wire and a coating disposed over the metal wire.

3. The two-dimensional resistance temperature detector of claim 1, wherein the insulated wire is arranged in a knitted pattern to form the mesh structure.

4. The two-dimensional resistance temperature detector of claim 1, wherein the two-dimensional resistance temperature detector has a first side and a second side disposed opposite the first side, and wherein the mesh structure defines a plurality of openings extending from the first side to the second side between adjacent sections of the insulated wire.

5. The two-dimensional resistance temperature detector of claim 4, wherein a maximum thickness of the two-dimensional resistance temperature detector between the first side and the second side is equal to twice a thickness of the insulated wire.

6. The two-dimensional resistance temperature detector of claim 4, wherein the insulated wire comprises a plurality of overlapping sections each having a first thickness and a plurality of non-overlapping sections each having a second thickness that is greater than the first thickness, and wherein a maximum thickness of the two-dimensional resistance temperature detector between the first side and the second side is less than twice the second thickness.

7. The two-dimensional resistance temperature detector of claim 4, wherein a thickness of the insulated wire between the first side and the second side is less than a width of the insulated wire along at least a portion of the insulated wire.

8. The two-dimensional resistance temperature detector of claim 1, wherein the two-dimensional resistance temperature detector is configured for positioning over the surface such that the insulated wire directly contacts the surface, and wherein the mesh structure is flexible such that the mesh structure is configured for conforming to a shape of the surface.

9. A method for determining average temperature over a surface, the method comprising:

positioning a two-dimensional resistance temperature detector over the surface such that each of a plurality of insulated wires of the two-dimensional resistance temperature detector directly contacts the surface, wherein the insulated wires are arranged to form a mesh structure with respective sections of each of the insulated wires overlapping and contacting one another, wherein the two-dimensional resistance temperature detector is devoid of any fabric material;

determining resistances of the insulated wires; and determining an average surface temperature based at least in part on the resistances of the insulated wires.

10. The method of claim 9, wherein the insulated wires are arranged in a knitted pattern to form the mesh structure.

11. The method of claim 9, wherein positioning the two-dimensional resistance temperature detector over the surface comprises positioning the two-dimensional resistance temperature detector over the surface such that a majority of a length of each of the insulated wires directly contacts the surface.

12. The method of claim 9, further comprising:

positioning a heating device or a cooling device over the surface; and causing a temperature setting of the heating device or the cooling device to change based at least in part on the average surface temperature.

13. The method of claim 12, further comprising causing a temperature setting of the heating device or the cooling device to change based at least in part on the average surface temperature, wherein the surface is an internal surface of a heating device or a cooling device.

14. A two-dimensional resistance temperature detector for determining average temperature over a surface, the two-dimensional resistance temperature detector comprising:

a plurality of insulated wires arranged to form a plurality of regions of the two-dimensional resistance temperature detector;

wherein each of the insulated wires has a first end and a second end and is arranged to form a mesh structure of a respective region of the plurality of regions, wherein the two-dimensional resistance temperature detector is devoid of any fabric material;

wherein the two-dimensional resistance temperature detector has a first side and a second side disposed opposite the first side; and wherein the regions do not overlap one another in a direction from the first side to the second side.

15. The two-dimensional resistance temperature detector of claim 14, wherein each of the insulated wires is arranged in a knitted pattern to form the mesh structure of the respective region.

16. The two-dimensional resistance temperature detector of claim 14, wherein each of the mesh structures defines a plurality of openings extending from the first side to the second side between adjacent sections of the respective insulated wire.

17. The two-dimensional resistance temperature detector of claim 16, wherein each of the insulated wires comprises a plurality of overlapping sections each having a first thickness and a plurality of non-overlapping sections each having a second thickness that is greater than the first thickness, and wherein a maximum thickness of the two-dimensional resistance temperature detector between the first side and the second side is less than twice the second thickness.

18. The two-dimensional resistance temperature detector of claim 14, wherein the two-dimensional resistance temperature detector is configured for determining average temperatures for respective regions of the surface, and wherein the regions of the two-dimensional resistance temperature detector correspond to the respective regions of the surface.

19. The two-dimensional resistance temperature detector of claim 18, wherein the two-dimensional resistance temperature detector is configured for determining an average temperature for the surface based at least in part on the average temperatures for the respective regions of the surface.

20. A system comprising:

the two-dimensional resistance temperature detector of claim 1;

a resistance module connected to the two-dimensional resistance temperature detector and configured to acquire resistance data for the two-dimensional resistance temperature detector;

one or more heating or cooling devices; and a controller in electrical communication with the resistance module and the one or more heating or cooling devices, wherein the controller is configured to determine an average surface temperature based on the resistance data, wherein the controller is configured to cause the one or more heating or cooling devices to change an applied temperature based at least in part on the average surface temperature.

* * * * *